(12) United States Patent
Busse et al.

(10) Patent No.: US 7,927,806 B2
(45) Date of Patent: *Apr. 19, 2011

(54) DISTINGUISHING PCA3 MESSENGER RNA SPECIES IN BENIGN AND MALIGNANT PROSTATE TISSUES

(75) Inventors: Ursula Busse, Saint-Louis (FR); Camille Chypre, Annecy (FR); Yves Fradet, Quebec (CA)

(73) Assignee: Diagnocure Inc., Sainte-Foy (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/635,917

(22) Filed: Dec. 11, 2009

(65) Prior Publication Data

US 2010/0129824 A1    May 27, 2010

Related U.S. Application Data

(60) Continuation of application No. 12/098,577, filed on Apr. 7, 2008, now Pat. No. 7,655,408, which is a division of application No. 09/675,650, filed on Sep. 29, 2000, now Pat. No. 7,368,545.

(60) Provisional application No. 60/156,594, filed on Sep. 29, 1999.

(51) Int. Cl.
*C12Q 1/68* (2006.01)
*C07H 21/04* (2006.01)

(52) U.S. Cl. ...... 435/6; 536/23.1; 536/24.31; 536/24.33

(58) Field of Classification Search .................. None
See application file for complete search history.

(56) References Cited

U.S. PATENT DOCUMENTS

| | | | |
|---|---|---|---|
| 4,581,333 A | 4/1986 | Kourilsky et al. |
| 4,683,195 A | 7/1987 | Mullis et al. |
| 4,683,202 A | 7/1987 | Mullis |
| 4,786,600 A | 11/1988 | Kramer et al. |
| 4,800,159 A | 1/1989 | Mullis et al. |
| 4,851,331 A | 7/1989 | Vary |
| 4,965,188 A | 10/1990 | Mullis et al. |
| 5,002,867 A | 3/1991 | Macevicz |
| 5,068,176 A | 11/1991 | Vijg et al. |
| 5,082,670 A | 1/1992 | Gage et al. |
| 5,112,736 A | 5/1992 | Caldwell et al. |
| 5,118,801 A | 6/1992 | Lizardi |
| 5,149,625 A | 9/1992 | Church et al. |
| 5,174,986 A | 12/1992 | Berns et al. |
| 5,175,383 A | 12/1992 | Leder et al. |
| 5,183,949 A | 2/1993 | Kindt et al. |
| 5,202,231 A | 4/1993 | Drmanac et al. |
| 5,219,989 A | 6/1993 | Sonenberg et al. |
| 5,283,174 A | 2/1994 | Arnold, Jr. et al. |
| 5,312,728 A | 5/1994 | Lizardi et al. |
| 5,399,491 A | 3/1995 | Kacian et al. |
| 5,422,252 A | 6/1995 | Walker et al. |
| 5,466,590 A | 11/1995 | Sariaslani et al. |
| 5,503,980 A | 4/1996 | Cantor |
| 5,547,842 A | 8/1996 | Hogan et al. |
| 5,554,516 A | 9/1996 | Kaclan et al. |
| 5,585,481 A | 12/1996 | Arnold, Jr. et al. |
| 5,593,974 A | 1/1997 | Rosenberg et al. |
| 5,639,604 A | 6/1997 | Arnold, Jr. et al. |
| 5,656,207 A | 8/1997 | Woodhead et al. |
| 5,658,737 A | 8/1997 | Nelson et al. |
| 5,674,682 A | 10/1997 | Croce et al. |
| 5,773,705 A | 6/1998 | Vierstra et al. |
| 5,837,832 A | 11/1998 | Chee et al. |
| 5,861,242 A | 1/1999 | Chee et al. |
| 5,925,517 A | 7/1999 | Tyagi et al. |
| 5,939,258 A | 8/1999 | Croce et al. |
| 6,037,130 A | 3/2000 | Tyagi et al. |
| 6,087,133 A | 7/2000 | Dattagupta et al. |
| 6,110,678 A | 8/2000 | Weisburg et al. |
| 6,261,562 B1 | 7/2001 | Xu et al. |
| 6,262,245 B1 | 7/2001 | Xu et al. |
| 6,280,952 B1 | 8/2001 | Weisburg et al. |
| 6,287,820 B1 | 9/2001 | Umansky et al. |
| 6,383,739 B1 | 5/2002 | Kurth et al. |
| 6,395,278 B1 | 5/2002 | Xu et al. |
| 6,465,611 B1 | 10/2002 | Xu et al. |
| 6,479,263 B1 | 11/2002 | Slawin et al. |
| 6,528,260 B1 | 3/2003 | Blumenfeld et al. |
| 6,534,273 B2 | 3/2003 | Weisburg et al. |

(Continued)

FOREIGN PATENT DOCUMENTS

EP    0125023    11/1984

(Continued)

OTHER PUBLICATIONS

Watala et al., "Multivariate relationships between international normalized ratio and vitamin K-dependent coagulation-derived parameters in normal healthy donors and oral anticoagulant therapy patients", Thrombosis Journal, 30;1(1):7 (2003).

Wei, C., et al., Tissue-specific expression of the human prostate-specific antigen gene in transgenic mice: Implications for tolerance and immunotherapy, Proc. Natl. Acad. Sci. USA 94:6369-6374, The National Academy of Sciences of the USA (1997).

Weiss, R., "Hot Prospect for New Gene Amplifier," Science 254:1292-1293, American Association for the Advancement of Science (1991).

(Continued)

*Primary Examiner* — Laura B Goddard
(74) *Attorney, Agent, or Firm* — Goudreau Gage Dubuc; Charles Goyer

(57) ABSTRACT

This invention concerns the discovery of two distinct PCA3 mRNA sequences. One of these sequences corresponds to a short PCA3 mRNA molecule whereas the other PCA3 RNA molecule is longer as it comprises an additional sequence between exon 3 and exon 4a. The short RNA is associated with prostate cancer whereas the long RNA sequence is associated with a non-malignant state of the prostate. Based on the differential expression levels of these two PCA3 RNA sequences, protocols for the diagnosis of prostate disease are provided. The invention also relates to therapeutic approaches to prostate cancer.

20 Claims, 4 Drawing Sheets

U.S. PATENT DOCUMENTS

| | | |
|---|---|---|
| 6,551,778 B1 | 4/2003 | Harvey et al. |
| 6,800,746 B2 | 10/2004 | Xu et al. |
| 6,897,024 B2 | 5/2005 | Bussemakers et al. |
| 7,008,765 B1 | 3/2006 | Bussemakers et al. |
| 7,138,235 B2 | 11/2006 | Bussemakers et al. |
| 7,368,545 B1 | 5/2008 | Busse et al. |
| 7,632,643 B2 | 12/2009 | Bussemakers et al. |
| 2002/0022248 A1 | 2/2002 | Xu et al. |
| 2002/0035244 A1 | 3/2002 | Cohen et al. |
| 2002/0168638 A1 | 11/2002 | Schlegel et al. |
| 2003/0165850 A1 | 9/2003 | Bussemakers et al. |
| 2005/0158792 A1 | 7/2005 | Bussemakers et al. |
| 2005/0164223 A1 | 7/2005 | Schalken et al. |
| 2005/0282170 A1 | 12/2005 | Fradet et al. |
| 2006/0099658 A1 | 5/2006 | Bussemakers et al. |
| 2010/0021884 A1 | 1/2010 | Hessels et al. |

FOREIGN PATENT DOCUMENTS

| | | |
|---|---|---|
| EP | 0160228 | 11/1985 |
| EP | 0171496 | 2/1986 |
| EP | 0173494 | 5/1986 |
| EP | 0184187 | 11/1986 |
| EP | 0256932 | 2/1988 |
| EP | 0520794 | 12/1992 |
| EP | 0320308 | 3/1993 |
| EP | 0747706 | 12/1996 |
| EP | 1295125 | 5/2006 |
| WO | WO 86/01533 | 3/1986 |
| WO | WO 87/02671 | 10/1986 |
| WO | WO 90/00944 | 2/1990 |
| WO | WO 91/19008 | 12/1991 |
| WO | WO 93/03743 | 4/1993 |
| WO | WO 93/08845 | 5/1993 |
| WO | WO 93/13121 | 7/1993 |
| WO | WO 94/09820 | 5/1994 |
| WO | WO 94/15646 | 7/1994 |
| WO | WO 95/28498 | 10/1995 |
| WO | WO 95/32305 | 11/1995 |
| WO | WO 96/11266 | 4/1996 |
| WO | WO 96/14875 | 5/1996 |
| WO | WO 96/32966 | 10/1996 |
| WO | WO 98/02582 | 1/1998 |
| WO | WO 98/45420 | 10/1998 |
| WO | WO 00/04149 | 1/2000 |
| WO | WO 00/50899 | 8/2000 |
| WO | WO 00/58470 | 10/2000 |
| WO | WO 01/23550 | 4/2001 |
| WO | WO 01/25272 | 4/2001 |
| WO | WO 01/25273 | 4/2001 |
| WO | WO 01/34802 | 5/2001 |
| WO | WO 01/44507 | 6/2001 |
| WO | WO 01/51633 | 7/2001 |
| WO | PCT/CA00/01154 | 8/2001 |
| WO | WO 01/60860 | 8/2001 |
| WO | WO 01/73032 | 10/2001 |
| WO | WO 02/24718 | 3/2002 |
| WO | WO 02/30268 | 4/2002 |
| WO | PCT/CA00/01154 | 8/2002 |
| WO | WO 2004/070056 | 8/2004 |

OTHER PUBLICATIONS

Xu et al., "Expression profile of an androgen regulated prostate specific homeobox gene NKX3.1 in primary prostate cancer". J Urol. 163:972-9 (2000).

Yelin et al., "Widespread occurrence of antisense transcription in the human 1, genome," Nat. Biotechnol. 21:379-386, Nature Publishing Group (Apr. 2003).

Ylikoski et al., "Dual-label detection of amplified products in quantitative RT-PCR assay using lanthanide-labeled probes". Biotechniques. 30:832-6, 838, 840 (2001).

Ylikoski et al., "Quantitative reverse transcription-PCR assay with an internal standard for the detection of prostate-specific antigen mRNA". Clin Chem. 45:1397-407 (1999).

Altschul, S.F., et al., "Gapped BLAST and PSI-BLAST: a new generation of protein database search programs," Nucl. Acids Res. 25:3389-3402, Oxford University Press (1997).

Armbruster et al., "Enzyme immunoassay, kinetic microparticle immunoassay, radioimmunoassay, and fluorescence polarization immunoassay compared for drugs-of-abuse screening", Clin Chem. 39(10):2137-46 (1993).

Arnold, Jr., L.J., et al., "Assay Formats Involving Acridinium-Ester-Labe/ed DNA Probes," Clin. Chem. 35:1588-1594, American Association for Clinical Chemistry (1989).

Auffray C, Rougeon F. "Purification of mouse immunoglobulin heavy-chain messenger RNAs from total myeloma tumor RNA". Eur J Biochem 1980;107:303-14.

Barbu V, Dautry F. "Northern blot normalization with a 28S rRNA oligonucleotide probe". Nucleic Acids Res 1989;17:7115.

Beduschi MC, Oesterling JE. "Percent free prostate-specific antigen: the next frontier in prostate-specific antigen testing". Urology 51:98-109 (1998).

Bernard PS, Wittwer CT. "Real-time PCR technology for cancer diagnostics". Clin Chem. 48:1178-85 (2002).

Black, D.L., "Mechanisms of Alternative Pre-Messenger RNA Splicing," Annu. Rev. Biochem. 72:291-336 (Feb. 2003).

Boom, R., et al., "Rapid and Simple Method for Purification of Nucleic Acids," J. Clin, Microbiol. 28:495-503, American Society for Microbiology (1990).

Boulikas, T., "Gene Therapy of Prostate Cancer: p53, Suicidal Genes, and Other Targets," Anticancer Res. 17:1471-1505, International Institute of Anticancer Research (1997).

Bowie, J.U., "Deciphering the Message in Protein Sequences: Tolerance to Amino Acid Substitutions," Science 247:1306-1311, American Association for the Advancement of Science (1990).

Brakebusch, C., et al., "Expression of the 90K Immunostimulator Gene Is Controlled by a Promoter with Unique Features," J. Biol. Chem. 272:3674-3682, The American Society for Biochemistry and Molecular Biology, Inc. (1997).

Brawer et al., "Screening for prostatic carcinoma with prostate specific antigen". J Urol 147:841-5 (1992).

Brawer MK. "Prostate-specific antigen". Semin Surg Oncol. 18:3-9 (2000).

Chitale and Khubchandani, "Interpretation of Prostatic Biopsies: A Review", The Internet Journal of Urology. 3(1), (2005).

Brinster et al., "Factors affecting the efficiency of introducing foreign DNA into mice by microinjecting eggs", PNAS. 82 (13):4438-4442 (1985).

Brown, A.M., "A step-by-step guide to non-linear regression analysis of experimental data using a Microsoft Excel spreadsheet," Comput. Methods Programs Biomed. 65:191-200, Elsevier Scientific Publishers (Jun. 2001).

Buck, G.A., et al., "Design Strategies and Performance of Custom DNA Sequencing Primers," BioTechniques 27:528-536, Informa Healthcare USA, Inc. (Sep. 1999).

Burgess, W.H., et al., "Possible Dissociation of the Heparin-binding and Mitogenic Activities of Heparin-binding (Acidic Fibroblast) Growth Factor-1 from its Receptorbinding Activities by Site-directed Mutagenesis of a Single Lysine Residue," J Cell. Biol. // / :2129-2138, The Rockefeller UMversity Press (1990).

Bussemakers et al., "DD3: a new prostate-specific gene, highly overexpressed in prostate cancer", Amer Assoc Cancer Research, 59:5975-9 (1999).

Bussemakers, M.J.G., et al., "DD3: a new prostate specific marker, overexpressed in prostatic tumors," Proc. Annu. Meet. Amer. Assoc. Cancer Res. 87:515, Abstract No. 3522, 87th Annual meeting of the American Association for Cancer Research (1996).

Bussemakers, M.J., and Isaacs, W.B., "Identification of Genes Associated with Prostate Cancer Development," Urol. Res. 21:452, Abstract No. P42, Springer International (1993).

Bussemakers, M.J.G., "Changes in Gene Expression and Targets for Therapy," Eur. Urol. 35:408-412, Elsevier Science (Jan. 1999).

Bussemakers, M.J.G., et al., "Assessment of the Clincial Usefulness of the Prostate-Cancer-Specific DD3 Gene," Eur. Urol. 36: 508, Abstract No. 0139, Elsevier Science (Nov. 1999).

Bussemakers, M.J.G., et al., "DD3: A New Prostate Specific Marker, Overexpressed in Prostatic Tumors," Presented at Breast and Prostate Cancer: Basic Mechanisms, Taos, New Mexico, Abstract No. 102, 1 page (Jan. 29-Feb. 4, 1996).

Bussemakers, M.J.G., et al., "DD3: A New Prostate Specific Marker, Overexpressed in Prostatic Tumors," Presented at Meeting for the Dutch Association for Tumor Cell Biology, May, The Netherlands, 1 page (1996).

Bussemakers, M.J.G., et al., "DD3: A New Prostate-Specific Marker, Strongly Overexpressed in Prostatic Tumors," Urol. Res. 25:76, Abstract No. 02.2, Springer International (1997).

Bussemakers, M.J.G., et al., "Identification of DD3: A New Gene Overexpressed in Prostatic Tumors," Urol. Res. 23:253, Abstract No. 0 36, Springer International (1995).

Bussemakers, MJ.G., and Isaacs, W.B., "Identification of Genes Associated with Prostate Cancer Development," Presented at 8th Annual Spring Meeting, May 13-May 14, San Fransico, CA, one page, Society for Basic Urologic Research (1994).

Bussemakers, MJ.G., et al., "DD3: A New Prostate Specific Marker, Overexpressed in Prostatic Tumors," Presented at Fall Symposium, Dec. 7-10, Chapel Hill, North Carolina, 1 page, Society for Basic Urologic Research (1995).

Bustin SA. "Absolute quantification of mRNA using real-time reverse transcription polymerase chain reaction assays", J Mol Endocrinol 2000;25:169-93.

Cairns, P., et al., "Molecular Detection of Prostate Cancer in Urine by GSTP1 Hypermethylation," Clin. Cancer Res. 7:2727-2730, The American Association for Cancer Research (Sep. 2001).

Catalona et al., "Measurement of prostate-specific antigen in serum as a screening test for prostate cancer". N Engl J Med, 324:1156-61 (1991).

Cheung, R.C., et al., "Rapid and Sensitive Method for Detection of Hepatitis C Virus RNA by Using Silica Particles," J. Clin. Microbiol. 10:2593-2597, American Society for Microbiology (1994).

Clements, J.A., et al., "Molecular Detection of Prostate Cells in Ejaculate and Urethral Washings in Men With Suspected Prostate Cancer," J. Urol. 161:1337-1343, Lippincott Williams & Wilkins (Apr. 1999).

Cleutjens, K.B.J.M., et al., "A 6-kb Promoter Fragment Mimics in Transgenic Mice the Prostate-Specific and Androgen-Regulated Expression of the Endogenous Prostate-Specific Antigen Gene in Humans," Mol. Endocrinol. I 1:1256-1265, The Endocrine Society (1997).

Cleutjens, K.B.J.M., et al., "An Androgen Response Element in a Far Upstream Enhancer Region Is Essential for High, Androgen-Regulated Activity of the Prostate-Specific Antigen Promoter," Mol. Endocrinol. 11:148-161, The Endocrine Society (1997).

Database EMBL Online, Bussemakers et al., Accession No. AF103908 (Nov. 1999).

Database NCBI Entrez, GenBank Report, Accession No. AL359314 (May 2001).

Database NCBI, Accession No. AF103907 (Aug. 2000).

Database NCBI, Accession No. AF103908 (Aug. 2000).

de Kok et al., DD3(PCA3), a very sensitive and specific marker to detect prostate tumors. Amer Assoc Cancer Res. 62:2695-8 (2002).

Deras et al., "PCA3: A molecular urine assay for preicting prostate biopsy outcome", J Urol 179:1587-1592 (2008).

Dieffenbach et al., "General concepts for PCR primer design", PCR Methods Appl. 3:30-37 (1993).

Edery, I., et al., "High-level synthesis in *Escherichia coli* of functional cap-binding eukaryotic initiation factor eIF-4E and affinity purification using a simplified cap-analog resin," Gene 74:517-525, Elsevier/North-Holland (1988).

El-Shirbiny, A.M., "Prostatic Specific Antigen," Adv. Clinical Chem. 31:99-133, Academic Press, Inc. (1994).

Ferrari AC, Stone NN, Eyler JN, Gao M, Mandeli J, Unger P et al. Prospective analysis of prostate-specific markers in pelvic lymph nodes of patients with high risk prostate cancer. J Natl Cancer Inst 1997;89:1498-504.

Fradet, Y., et al., "uPM3, A Molecular Urine Test for the Detection of Prostate Cancer," Urology 64: 311-316, Elsevier Science Ltd. (Aug. 2004).

Friedmann, T., "Overcoming the Obstacles to Gene Therapy," Sci. Am. 276:96-101, Scientific American (1997).

Murphy et al., "Evaluation and comparison of two new prostate carcinoma markers. Freeprostate specific antigen and prostate specific membrane antigen". Cancer. 78:809-18 (1996).

Nelson et al., "Molecular cloning and characterization of prostate, an androgen-regulated serine protease with prostate-restricted expression". Proc Natl Acad Sci USA 96:3114-9 (1999).

Nielsen, P.E., "Applications of peptide nucleic acids," Curr. Opin. Biotechnol. 10:71-75, Elsevier Science Ltd. (Feb. 1999).

Nixon RG, Brawer MK. Enhancing the specificity of prostate-specific antigen (PSA): an overview of PSA density, velocity and age-specific reference ranges. Br J Urol 1997;79 Suppl 1:61-7.:61-7.

Nurmi et al., "High-performance real-time quantitative RT-PCR using lanthanide probes and a dual-temperature hybridization assay". Anal Chem 2002;74:3525-32.

Oettgen et al., "PDEF, a novel prostate epithelium-specific ets transcription factor, interacts with the androgen receptor and activates prostate-specific antigen gene expression". J Biol Chem 275:1216-25 (2000).

Office Action for U.S. Appl. No. 09/996,953, inventors Bussemakers, M.J., et al., filed Nov. 30, 2001, mailed on Aug. 26, 2003.

Pang, S., et al., "Identification of a Positive Regulatory Element Responsible for Tissue-specific Expression of Prostate-specific Antigen," Cancer Res. 57:495-499, The American Association for Cancer Research (1997).

Partin et al., "Complexed Prostate Specific Antigen Improves Specificity for Prostate Cancer Detection: Results of a Prospective Multicenter Clinical Trial", Journal of Urology, 170(5):1787-1791 (2003).

Paule MR, White RJ. Survey and summary: transcription by RNA polymerases I and I II. Nucleic Acids Res 2000;28:1283-98.

Polascik et al., "Prostate specific antigen: a decade of discovery—what we have learned and where we are going". J Urol. 62:293-306 (1999).

Quandt, K., et al., "MatInd and MatInspector: new, fast and versatile tools for detection of consensus matches in nucleotide sequence data," Nucl. Acids Res. 23:4878-4884, Oxford University Press (1995).

Raeymaekers L. "Quantitative PCR: theoretical considerations with practical implications". Anal Biochem. 214:582-5 (1993).

Rieger-Christ, K., et al., "Identification of Fibroblast Growth Factor Receptor 3 Mutations in Urine Sediment DNA Samples Complements Cytology in Bladder Tumor Detection," Cancer 98:737-744, American Cancer Society (Aug. 2003).

Ringsrud, K.M., "Cells in the Urine Sediment," Lab. Med. 32:153-155, American Society for Clinical Pathology (Mar. 2001).

Rubanyi, G.M., "The future of human gene therapy," Mol. Aspects Med. 22:113-142, Elsevier Science (Jun. 2001).

Rubin and Levy, "A mathematical model and a computerized simulation of PCR using complex templates", Nucleic Acids Research, 24(18):3538-3545 (1996).

Rychlik and Rhaods, "A computer program for choosing optimal oligonucleotides for filter hybridization, sequencing and in vitro amplification of DNA", Nucleic Acids Research, 17(21):8543-8551 (1989).

Rychlik, W, "Chapter 2: Selection of primers for polymerase chain reaction", from Methods in Molecular Biology vol. 15. PCR Protocols: Current methods and applications. Ed. Bruce A, White, Humana Press Inc, pp. 31-40 (1993).

Schalken et al., "New targets for therapy in prostate cancer: Differential display code 2 (DD3(PCA3)), a highly prostate cancer-specific gene", Urology 62(Suppl. 5A):34-43 (2003).

Schalken, J., "Molecular Diagnostics and Therapy of Prostate Cancer: New Avenues," Eur. Urol. 34 Suppl 3:3-6, S. Karger AG (1998).

Schuur, E.R., et al., "Prostate-specific Antigen Expression Is Regulated by an Upstream Enhancer," J. Biol. Chem. 271:7043-7051, The American Society for Biochemistry and Molecular Biology, Inc. (1996).

Schwartz, C.J., et al., "FTZ-Factorl and *Fushi tarazu* interact via conserved nuclear receptor and coactivator motifs," EMBO J 20:510-519, Oxford University Press (Feb. 2001).

Sequence Comparisions in Office Action for U.S. Appl. No. 10/773,440, inventors Fradet, Y. et al., filed Feb. 9, 2004, mailed on Jun. 23, 2006.

Sharrocks, AD, "Chapter 2: The design of primers for PCR", from PCT Technology Current Innovations. Eds. Hugh G, Griffin and Annette M. Griffin. CRC Press pp. 5-11 (1994).

Sidransky, D., "Nucleic acid-based methods for the detection of cancer", Science, 278(5340):1054-9 (1997).
Smith et al., "Prostate-specific antigen messenger RNA is expressed in non-prostate cells: implications for detection of micrometastases". Cancer Res. 55:2640-4 (1995).
Soini E, Lovgren T. "Time-resolved fluorescence of lanthanide probes and applications in biotechnology". CRC Crit Rev Anal Chem. 18:105-54 (1987).
Srikantan et al., "PCGEM1, a prostate-specific gene, is overexpressed in prostate cancer". Proc Natl Acad Sci USA Oct. 24, 2000;97(22):12216-21 2001;97:12216-21.
Strickler, H.D., and International SV40 Working Group, "A Multicenter Evaluation of Assays for Detection of SV40 DNA and Results in Masked Mesothelioma Specimens," Cancer Epiderniol. Biomarkers Prev. 10:523-532, American Association for Cancer Research (May 2001).
Sun Y, Lin J, Katz AE, Fisher PB. Human prostatic carcinoma oncogene PTI-1 is expressed in human tumor cell lines and prostate carcinoma patient blood samples. Cancer Res 1997;57:18-23.
Sutcliffe, J.G. et al., "Antibodies That React with Predetermined Sites on Proteins," Science 219:660-666, Association for the Advancement of Science (1983).
Syfpeithi at http://134.2.96.221/scripts/MHCServer,d11/home.htm (Mar. 13, 2001).
Tamimi, Y., et al., "DiagnoGene PCA3 reliable NASBA based reagents for detecting PCA3 niRNA, a recently described prostate marker," Proc. Am. Assoc. Cancer Res. 39:234 Poster Abstract, Williams & Wilkins (Mar. 1998).
Taneja, S.S., et al., "Chapter 23: Gene Therapy: Principles and Potential, in Cancer Surveys: Preventing Prostate Cancer: Screening versus Chemoprevention," Oliver, R.T.D., et al., eds., Cold Spring Harbor Laboratory Press, pp. 247-266 (1995).
Tinzl et al., "DD3 PCA3 RNA analysis in urine—a new perspective for detecting prostate cancer." European Urology. 46(2):182-186 (2004).
Tockman, M.S., et al., "Considerations in Bringing a Cancer Biomarker to Clinical Application," Cancer Res. 52:2711s-2718s, American Association for Cancer Research (1992).
Torres and Marks, "PCS3: A genetic marker of prostate cancer", PCRI Insights. New developments in prostate cancer treatment. 9(3):4-9 (2006).
Tyagi, S., and Kramer, F.R., "Molecular Beacons: Probes that Fluoresce upon Hybridi7ation," Nat. Biotechnol. 14:303-308, Nature Publishing Group (1996).
Ukimura et al., "Role of PSA and its indices in determining the need for repeat prostate biopsies". Urology 1997;50:66-72.
Vallejo et al., "In vitro synthesis of novel genes: mutagenesis and recombination by PCR", PCR Methods Appl. 4:123-130 (1994).
Vandesompele et al., "Accurate normalization of real-time quantitative RT-PCR data by geometric averaging of multiple internal control genes". Genome Biol 3: RESEARCH0034 (2002).
Verhaegh, G.W., et al., "Characterization of the Prostate-Cancer-Specific DD3 Gene Promoter," Eur. Urol. 38:490, Abstract 10, S. Karger (Oct. 2000).
Verhaegh, G.W., et al., "Isolation and Characterization of the Promoter of the Human Prostate Cancer-specific DD3 Gene," J. Biol. Chem. 275:37496-37503, The American Society for Biochemistry and Molecular Biology (Dec. 2000).
Verkaik, N.S. et al., "Clinical usefulness of RT-PCR detection of hematogenous prostate cancer spread," Urol. Res. 25:373-384, Springer-Verlag (1997).
Verma, I.M., and Somia, N., "Gene therapy—promises, problems and prospects", Nature 389:239-242, Nature Publishing Group (1997).
Voet, D., and Voet, J.G., eds., "Chapter 28: Nucleic Acid Structures and Manipulation," in Biochemistry, 1st Ed., John Wiley & Sons, Inc., San Francisco, CA (1990).
Walker, G.T., et al., "Isothermal in vitro amplification of DNA by a restriction enzyme/DNA polymerase system," Proc, Natl. Acad. Sci. US.A. 89:392-396, National Academy of Sciences (1992).
Walker, G.T., et al., "Strand displacement amplification—an isothermal, in vitro DNA amplification technique," Nucleic Acids Res. 20:1691-1696, Oxford University Press (1992).

Gandini et al., "Is DD3 a New Prostate-Specific Gene?," Anticancer Res. 23:305-308, Anticancer Research (Jan.-Feb. 2003).
Gen-Probe Brochure, "Prostate Cancer Gene 3 (PCA3): the new tool available to improve the diagnosis of prostate cancer in a simple urine test", Gen_Probe Incorporated (2007).
Gibson et al., "A novel method for real time quantitative RT-PCR". Genome Res. 6:995-1001 (1996).
Goessl et al., "A DNA-Based Method for Detection of Prostate Cancer Cells in Urine After Prostatic Massage," Eur. Urol. Suppl. 1:32, article 118, Elsevier Science (Jan. 2002).
Goessl et al., "DNA-Based Detection of Prostate Cancer in Urine After Prostatic Massage," Urology 58:335-338, Elsevier Science (Sep. 2001).
Goessl et al., "Fluorescent Methylation-specific Polymerase Chain Reaction for DNA-based Detection of Prostate Cancer in Bodily Fluids," Cancer Res. 60:5941-5945, American Association for Cancer Research (Nov. 2000).
Goldman et al., "Can prostate-specific antigen reverse transcriptase-polymerase chain reaction be used as a prospective test to diagnose prostate cancer?" World J Urol. 15:257-61 (1997).
Gomella et al., "Reverse Transcriptase Polymerase Chain Reaction for Prostate Specific Antigen in the Management of Prostate Cancer," J. Urology 158:326-337, American Urological Association, Inc. (1997).
Gotoh, A., et al., "Development of Prostate-Specific Antigen Promoter-Based Gene Therapy for Androgen-Independent Human Prostate Cancer," J. Urol. 160:220-229, American Urological Association, Inc. (Jul. 1998).
Grasso et al., "Combined nested RT-PCR assay for prostate-specific antigen and prostate-specific membrane antigen in prostate cancer patients: correlation with pathological stage". Cancer Res. 58:1456-9 (1998).
Grayburn and Sims, "Anchored Oligo(dT) Primers for Automated Dye Terminator DNA Sequencing", BioTechniques. 25(3):340-346 (1998).
Gu et al., "Prostate stem cell antigen (PSCA) expression increases with high gleason score, advanced stage and bone metastasis in prostate cancer". Oncogene. 19:1288-96 (2000).
Guichet et al., "The nuclear receptor homologue Ftz-F1 and the homeodomain protein Ftz are mutually dependent cofactors," Nature 385:548-552, Nature Publishing Group (1997).
Hessels, D., et al. "DD3Pcm-based Molecular Urine Analysis for the Diagnosis of Prostate Cancer," Eur. Urol. 44:8-15, Elsevier Science (Jul. 2003).
Hillier and Green, "OSP: A computer program for choosing PCR and DNA sequenceing primers", PCR Methods Appl. 1:124-128 (1991).
Horninger et al., "Complexed prostate-specific antigen for early detection of prostate cancer in men with serum prostate-specific antigen levels of 2 to 4 nanograms per milliliter." Urology. 60(4):31-35 (2002).
Houdebine, L-M., "Production of pharmaceutical proteins from transgenic animals," J. Biochem. 34:269-287, Oxford University Press (1994).
Hsing, A.W., et al., "International Trends and Patterns of Prostate Cancer Incidence and Mortality," Int J. Cancer 85:60-67, Wiley-Liss, Inc., (Jan. 2000).
Ingelfinger, R.J., "Nephrogenic Adenomas as Renal Tubular Outposts," N. Engl. J. Med. 347:684-686, Massachusetts Medical Society (Aug. 2002).
Israeli et al., "Sensitive Nested Reverse Transcription Polymerase Chain Reaction Detection of Circulating Prostatic Tumor Cells: Comparison of Prostate-specific Membrane Antigen and Prostatespecific Antigen-based Assays," Cancer Res. 54:6306-6310, American Association for Cancer Research (1994).
Iwakiri, J., et al., "An Analysis of Urinary Prostate Specific Antigen Before and After Radical Prostatectomy: Evidence for Secretion of Prostate Specific Antigen by the Periurethral Glands," J. Urol. 149:783-786, Elsevier Science Ltd. (1993).
Jensen et al., "Cancer in the European Community and its member states". Eur J Cancer 26:1167-256 (1990).
Journal Sentinel wire reports, "Prostate blood test may but down on biopsies", May 20, 1998.

Kamoi K, Babaian RJ. "Advances in the application of prostate-specific antigen in the detection of early-stage prostate cancer". Semin Oncol, 26:140-9 (1999).

Katz et al., "Enhanced reverse transcriptase-polymerase chain reaction for prostate specific antigen as an indicator of true pathologic stage in patients with prostate cancer". Cancer. 75:1642-8 (1995).

Katz et al., "Molecular staging of prostate cancer with the use of an enhanced reverse transcriptase-PCR assay". Urology 1994;43:765-75.

Kirby, R.S., "Pre-treatment staging of prostate cancer: recent advances and future prospects," Prostate Cancer and Prostatic Dis. 1:2-10, Stockton Press (1997).

Kwoh, D.Y., et al., "Transcription-based amplification system and detection of amplified human immunodeficiency virus type 1 with a bead-based sandwich hybridization format," Proc. Natl. Acad. Sci. USA. 86:1173-1177, National Academy of Sciences (1989).

Kwok et al., "A guide to the design and use of mismatched and degenerate primers", PCR Methods Appl. 3:39-47 (1994).

Landis et al., "Cancer Statistics, 1998", CA Cancer J Clin 48(1):6-29 (1998).

Landis et al., "Cancer Statistics, 1999," CA Cancer J. Clin. 49:8-31, Lippincott Williams & Wilkins (Jan.-Feb. 1999).

Lange, P.H., "Chapter 41. Tumor Markers in Prostate Cancer," in: Principles and Practice of Genitourinary Oncology, Raghaven, D. et al., eds., Lippincott-Raven Publishers, Philadelphia, PA, pp. 417-425 (1997).

Lathe, R., "Synthetic Oligonucleotide Probes Deduced from Amino Acid Sequence Data Theoretical and Practical Considerations," J. Mol. Biol. 183:1-12, Academic Press (1985).

Lazar, E., et al., "Transforming growth factor a: mutation of aspartic acid 47 and leucine 48 results in different biological activities," Mol. Cell Biol. 8:1247-1252, American Society for Microbiology (1988).

Letran, J.L. et al., "Repeat Ultrasound Guided Prostate Needle Biopsy: Use of Free-To-Total Prostate Specific Antigen Ratio in Predicting Prostatic Carcinoma," J. Urology 160:426-429, American Urological Association, Inc. (Aug. 1998).

Lin et al., "Prostatelocalized and androgen-regulated expression of the membrane-bound serine protease TMPRSS2". Cancer Res. 59:4180-4 (1999).

Lintula S, Stenman UH. "The expression of prostate-specific membrane antigen in peripheral blood leukocytes". J Urol. 157:1969-72 (1997).

Lizardi, P., et al., "Exponential Amplification of Recombinant-RNA Hybridization Probes," BioTechnology 6:1197-1202, Nature Publishing Group (1988).

Lowe et al., "A computer program for selection of oligonucleotide primers for polymerase chain reactions", Nucleic Acids Research. 18(7):1757-1761 (1990).

Malek, L., et al., "Nucleic Acid Sequence-Based Amplification (NASBA)," Methods Mol. Biol. 28:253-260, Humana Press (1994).

Marks et al., "PCA3 molecular urine assay for prostate cancer in men undergoing repeat biopsy", Adult Urology, 69 (3):532-535(2007).

Martiniello-Wilks, R., et al.,"In Vivo Gene Therapy for Prostate Cancer: Preclinical Evaluation of Two Different Enzyme-Directed Prodrug Therapy Systems Delivered by Identical Adenovirus Vectors," Hum. Gene Ther. 9:1617-1626, Maty Ann Liebert, Inc. (Jul. 1998).

Matteucci, M.D., and Caruthers, M.H., "Synthesis of Deoxyoligonucleotides on a Polymer Support," J. Am. Chem. Soc. 103:3185-3191, American Chemical Society (1981).

Merriam-Webster Online Dictionary, definition for "kit" (Accessed Dec. 2005).

Mettlin et al., "The National Cancer Data Base report on longitudinal observations on prostate cancer". Cancer 77:2162-6 (1996).

Miller, P.S., and Ts'o, P.O.P., "Chapter 30: Oligonucleotide Inhibitors of Gene Expression in Living Cells: New Opportunities in Drug Design," Annu. Rep. Med, Chem. 23:295-304, Academic Press (1988).

Millikan, R.E., "Chemotherapy of Advanced Prostatic Carcinorna," Semin. Oncol. 26:185-191, W.B. Saunders Company (Apr. 1999).

Mintun et al., "Increased lactate pyruvate ratio augments blood flow in physiologically activated human brain", 101 (2):659-664 (2004).

Morvan, F., et al., "a-DNA. L Synthesis, characterization by high field III-NMR, and base-pairing properties of the unnatural hexadeoxyribonucleotide a-[d(CpCpTpTpCpC)] with its complement P-[d(GpGpApApGpG)]," Nucleic Acids Res. 14:5019-5035, Oxford University Press (1986).

Muller and Brenner, "Urine Markers as Possible Tools for Prostate Cancer Screening: Review of Performace Characteristics and Practicality", Clinical Chemistry, 524:562-573 (2006).

SEQ ID NO:1:

5'- CAGGAAGCAC AAAAGGAAGC ACAGAGgtaagtgctttata
aagcactcaatttctactca gaaatttttg atggccttaa gttcctctac tcgtttctat ccttcctact
cactgtcctc ccggaatcca ctaccgattt tctatttctt gcctcgtatt gtctgactgg ctcacttgga
tttatcctca cggagtctgg attttctacc cgggctcacc tccgtccctc catatttgtc ctccactttc
acagATCCCT GGGAGAAATG CCCGGCCGCC ATCTTGGGTC
ATCGATGAGC CTCGCCCTGT GCCTGGTCCC GCTTGTGAGG
GAAGGACATT AGAAAATGAA TTGATGTGTT CCTTAAAGGA
TGGGCAGGAA AACAGATCCT GTTGTGGATA TTTATTTGAA
CGGGATTACA GATTTGAAAT GAAGTCACCA AAGTGAGCAT
TACCAATGAG AGGAAAACAG ACGAGAAAAT CTTGAT**GGCT
TCACAAGACA TGCAAC**-3'

SEQ ID NO:2:

5'- CAGGAAGCA CAAAAGGAAG CACAGAGATC CCTGGGAGAA
ATGCCCGGCC GCCATCTTGG GTCATCGATG AGCCTCGCCC
TGTGCCTGGT CCCGCTTGTG AGGGAAGGAC ATTAGAAAAT
GAATTGATGT GTTCCTTAAA GGATGGGCAG GAAAACAGAT
CCTGTTGTGG ATATTTATTT GAACGGGATT ACAGATTTGA
AATGAAGTCA CCAAAGTGAG CATTACCAAT GAGAGGAAAA
CAGACGAGAA AATCTTGATG GCTTCACAAG ACATGCAAC - 3'

FIG. 3

MFLHISSPFKYPHTQEAQKEAQR*

FIG. 4

| | | |
|---|---|---|
| C-terminal/mouse: | AA 39-46 | LALCLVPL |
| | AA 26-33 | GEMPGRHL |
| C-terminal/human: | AA 33-40 | LGSSMSLA |
| | AA 44-51 | VPLVREGH |
| N-terminal/mouse: | AA 7-14 | SPFKYPHT |
| | AA 15-22 | QEAQKEAQ |
| N-terminal/human: | AA 14-21 | TQEAQKEA |
| | AA 2-9 | FLHISSPF |

SEQUENCE LISTING

<160> NUMBER OF SEQ ID NOS: 12

<210> SEQ ID NO 1
<211> LENGTH: 506
<212> TYPE: DNA
<213> ORGANISM: Homo sapiens

<400> SEQUENCE: 1

```
caggaagcac aaaaggaagc acagaggtaa gtgctttata aagcactcaa tttctactca      60
gaaatttttg atggccttaa gttcctctac tcgtttctat ccttcctact cactgtcctc     120
ccggaatcca ctaccgattt tctatttctt gcctcgtatt gtctgactgg ctcacttgga     180
tttatcctca cggagtctgg attttctacc cgggctcacc tccgtccctc catatttgtc     240
ctccactttc acagatccct gggagaaatg cccggccgcc atcttgggtc atcgatgagc     300
ctcgccctgt gcctggtccc gcttgtgagg gaaggacatt agaaaatgaa ttgatgtgtt     360
ccttaaagga tgggcaggaa aacagatcct gttgtggata tttatttgaa cgggattaca     420
gatttgaaat gaagtcacca aagtgagcat taccaatgag aggaaaacag acgagaaaat     480
cttgatggct tcacaagaca tgcaac                                          506
```

<210> SEQ ID NO 2
<211> LENGTH: 278
<212> TYPE: DNA
<213> ORGANISM: Homo sapiens

<400> SEQUENCE: 2

```
caggaagcac aaaaggaagc acagagatcc ctgggagaaa tgcccggccg ccatcttggg      60
tcatcgatga gcctcgccct gtgcctggtc ccgcttgtga gggaaggaca ttagaaaatg     120
aattgatgtg ttccttaaag gatgggcagg aaaacagatc ctgttgtgga tatttatttg     180
aacgggatta cagatttgaa atgaagtcac caaagtgagc attaccaatg agaggaaaac     240
agacgagaaa atcttgatgg cttcacaaga catgcaac                            278
```

<210> SEQ ID NO 3
<211> LENGTH: 23
<212> TYPE: PRT
<213> ORGANISM: Homo sapiens

<400> SEQUENCE: 3

Met Phe Leu His Ile Ser Ser Pro Phe Lys Tyr Pro His Thr Gln Glu
1               5                   10                  15

Ala Gln Lys Glu Ala Gln Arg
            20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4

```
gagtaggaag gatagaaacg                                                  20
```

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: PCA3
      epitope

<400> SEQUENCE: 5

Leu Ala Leu Cys Leu Val Pro Leu
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: PCA3
      epitope

<400> SEQUENCE: 6

Gly Glu Met Pro Gly Arg His Leu
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: PCA3

```
                                    epitope

<400> SEQUENCE: 7

Leu Gly Ser Ser Met Ser Leu Ala
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: PCA3
      epitope

<400> SEQUENCE: 8

Val Pro Leu Val Arg Glu Gly His
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: PCA3
      epitope

<400> SEQUENCE: 9

Ser Pro Phe Lys Tyr Pro His Thr
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: PCA3
      epitope

<400> SEQUENCE: 10

Gln Glu Ala Gln Lys Glu Ala Gln
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: PCA3
      epitope

<400> SEQUENCE: 11

Thr Gln Glu Ala Gln Lys Glu Ala
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: PCA3
      epitope

<400> SEQUENCE: 12

Phe Leu His Ile Ser Ser Pro Phe
1               5
```

DISTINGUISHING PCA3 MESSENGER RNA SPECIES IN BENIGN AND MALIGNANT PROSTATE TISSUES

CROSS REFERENCE TO RELATED APPLICATIONS

This application is a continuation of U.S. application Ser. No. 12/098,577 filed Apr. 7, 2008, now U.S.Pat. No. 7,655,408, which itself is a divisional of U.S. patent application Ser. No. 09/675,650, filed Sep. 29, 2000 now U.S. Pat. No. 7,368,545, which claims priority to U.S. provisional application Ser. No. 60/156,594 filed Sep. 29, 1999. The patent applications identified above are incorporated here by reference in their entirety to provide continuity of disclosure.

SEQUENCE LISTING

This application contains a Sequence Listing in computer readable form entitled "Sequence Listing", created Dec. 2, 2009, having a size of 4 Ko. The computer readable form is incorporated herein by reference.

FIELD OF THE INVENTION

The present invention relates to prostate cancer. More specifically, the present invention relates to nucleic acid molecules (messenger RNAs) encoded by the gene PCA3; the differential expression of two of these RNA species in non-malignant and malignant prostatic states; methods for specifically diagnosing prostate cancer based on the detection of the RNA species related to prostate cancer; therapeutic approaches to prostate cancer implying these two RNA species; nucleic acid molecules and antibodies having binding affinity for the differentially expressed mRNAs; kits containing nucleic acid probes or antibodies; bioassays using the nucleic acid sequences of the differentially expressed mRNAs of the present invention to diagnose, assess or prognose a mammal afflicted with or susceptible to developing prostate cancer; and to bioassays to screen for compounds which modulate the expression of the mRNAs of the present invention.

BACKGROUND OF THE INVENTION

Over the last decade, cancer of the prostate has become the most commonly diagnosed malignancy among men and the second leading cause of male cancer deaths in the western population, following lung cancer (Landis et al., 1998, CA Cancer J. Clin. 48(1):6-29). Of all cancers, the incidence of prostate cancer increases most rapidly with age. As longevity among the western population increases, there continues to be a corresponding rise in the number of prostate cancers with an expected increase of 60% in this decade alone. Mortality has increased at a slower rate, but overall has doubled in the last 50 years. Although the disease is typically diagnosed in men over the age of 65, its impact is still significant in that the average life span of a man who dies from prostate cancer is reduced by 9-10 years. If discovered, early prostate cancer can now be cured with surgery in approximately 90% of cases. Unfortunately the disease is slowly fatal once the tumor spreads outsize the area of the gland and forms distant metastases. Early detection of the disease, while still confined to the prostate gland, and accurate staging for the selection of appropriate therapy should improve mortality rates.

Despite many advances in recent years, the precision with which an individual suffering from prostate cancer can be staged is still sub-optimal. The main reason for this is that tumor spread beyond the prostate is generally microscopic rather than macroscopic. Digital rectal examination of the prostate has been the cornerstone for the local staging of prostatic cancer for many decades, but it oftentimes underestimates the extent of the disease. Transrectal ultrasound by itself is only of limited value as a means of prostate cancer staging. Computer tomography and magnetic resonance imaging have generally been disappointing in the staging of prostate cancer (Kirby, 1997, Prostate cancer and Prostatic Diseases 1:2-10). Recent promising approaches to prostate cancer staging imply the use of biochemical and molecular technologies, centered around proteins or their corresponding nucleic acids which are preferentially expressed in prostate cells (Lange, 1997, In Principles and Practice of Genitourinary Oncology ed. Lippincott-Raven Publishers, Ch. 41, pp. 417-425). The most notorious prostate markers are PSA (prostate specific antigen) and PSM (prostate specific membrane) antigen.

PSA is a secreted glycoprotein encoded by the PSA gene located on chromosome 19. It is expressed under androgen control by glandular epithelial cells of the prostate and secreted into seminal plasma. PSA protein is normally confined to the prostate but in the case of prostatic disease such as cancer or BPH (benign prostate hyperplasia), PSA leaks into the blood where it is present in different forms, including one that is and one that is not bound to protein complexes (EI-Shirbiny, 1994, Adv. Clin. Chem. 31:99). The measurement of total PSA serum concentrations is one of the most frequently used and FDA-approved biochemical tests in the screening and management of prostate cancer patients. Studies to date have suggested that screening with PSA, in conjunction with digital rectal exams and transrectal ultrasound, increases the detection of early prostate cancers often while still localized to the gland itself (Brawer et al., 1992, J. Urol. 147:841). Serum PSA is also useful for monitoring of patients after therapy, especially after surgical prostatectomy. However, total PSA measurements also identify a large number of patients with abnormally elevated levels who are subsequently found to have no prostate cancer. Recently, the concept of measuring the percent free/total PSA ratio was shown to increase the specificity of prostate cancer screening in men with PSA between 4 and 10 ng/mL (Letran et al., 1998, J. Urol. 160:426).

The PSM gene encodes a transmembrane glycoprotein expressed by epithelial cells of normal prostate, benign prostate hyperplasia and, to a greater extent, malignant prostatic tissue. Low levels of PSM are also detected in some other tissues (Israeli et al., 1994, Cancer Res. 54:1807). PSA and PSM have also been targets for molecular approaches to prostate cancer using RT-PCR (reverse transcription -polymerase chain reaction). This very sensitive nucleic acid amplification technology is used to identify cells based on the expression of specific messenger RNAs. It involves preparing RNA samples from tissues or body fluids, reverse transcribing it into cDNA and amplifying specific cDNAs by the use of primers that target the particular gene of interest. RT-PCR analyses of blood, lymph nodes and bone marrow from prostate cancer patients using PSA and PSM have disclosed the extreme sensitivity of this approach. However, the clinical value of molecular tests still has to be confirmed (Verkaik et al., 1997, Urol. Res. 25:373; Gomella et al., 1997, J. Urol. 158:326).

Thus, there remains a need to provide a more sensitive test for diagnosing prostate cancer. There also remains a need to provide a better test for the staging of prostate cancer. There also remains a need to provide a prostate cancer marker which is more specific and more reliable to prostate cancer detection, staging and treatment methods.

The present invention seeks to meet these and other needs.

A new prostate cancer marker, PCA3, was discovered a few years ago by differential display analysis intended to highlight genes associated with prostate cancer development (PCT application number PCT/CA98/00346). PCA3 is located on chromosome 9 and composed of four exons. It encodes at least four different transcripts which are generated by alternative splicing and polyadenylation. By RT-PCR analysis, PCA3 expression was found to be limited to the prostate and absent in all other tissues, including testis, ovary, breast and bladder. Northern blot analysis showed that PCA3 is highly expressed in the vast majority of prostate cancers examined (47 out of 50) whereas no or very low expression is detected in benign prostate hyperplasia or normal prostate cells from the same patients. There is at least 20-fold overexpression of PCA3 in prostatic carcinomas in comparison to normal or BPH tissues. PCA3 expression seems to increase with tumor grade and is detected in metastatic lesions.

In summary, prostate cancer staging based on specific markers such as PSA and PSM is a very promising avenue for the management of the disease. The drawback of using PSA or PSM for prostate cancer staging is that they are expressed in normal as well as in cancerous cells. In addition, poorly differentiated tumors may escape diagnosis since they tend to produce significantly less PSA protein than less aggressive tumors. This is the case for 10% of all prostate cancers. PCA3, on the other hand, is differentially expressed in cancerous and normal prostate cells, and its expression does not decrease with increasing tumor grade. PCA3 could therefore be a useful tool which may overcome the drawbacks of PSA and PSM in the diagnosis, staging and treatment of prostate cancer patients.

The present description refers to a number of documents, the content of which is herein incorporated by reference, in their entirety.

SUMMARY OF THE INVENTION

The invention concerns the discovery of distinct PCA3 RNAs associated with a non-malignant and/or malignant status of the prostate.

The invention also concerns the identification that a balance between the level of these PCA3 mRNAs correlates with the non-malignant or the malignant status of the prostate.

One of these RNAs corresponds to a PCA3 RNA molecule having an additional sequence of 228 by (shown in SEQ ID NO:1), inserted between exons 3 and 4a, whereas the other lacks the additional sequence (SEQ ID NO:2). The RNA lacking the additional sequence is associated with prostate cancer whereas the RNA comprising same is associated with a non-malignant prostatic state. Based on the differential expression of these two PCA3 RNA species, protocols for the diagnosis of prostate disease are proivded. The above findings could also lead to a therapeutic approach to prostate cancer.

The invention further concerns reagents and methods to assess the prostate status in an animal, comprising a quantitative determination of SEQ ID NO:1 or fragments, or variants thereof with respect to SEQ ID NO:2 or fragments, or variants thereof.

Thus, the present invention relates to the discovery and characterization of a novel sequence expressed in PCA3 mRNA, which enables a determination of the prostate status of an animal, based on a determination of the relative abundance of two differentially expressed PCA3 mRNAs.

The invention provides, in general, isolated nucleic acid molecules encoding differentially expressed PCA3 mRNAs and to variants or portions thereof, retaining their ability to enable a prostate status determination.

The invention further provides purified polypeptides encoded by the differentially expressed PCA3 mRNAs of the present invention or an epitope binding portion thereof.

The invention also provides nucleic acids for the specific detection of the presence of differentially expressed PCA3 mRNAs associated with prostate cancer or proteins or polypeptides encoded by such mRNAs in a sample.

The invention further provides a method of detecting nucleic acid encoding differentially expressed PCA3 mRNAs.

The invention also provides a kit for detecting the presence of nucleic acid encoding differentially-expressed PCA3 mRNAs in a sample.

The invention in addition provides a recombinant nucleic acid molecule comprising, 5' to 3', a promoter effective to initiate transcription in a host cell and the above-described isolated nucleic acid molecule, variants or fragments thereof, encoding differentially expressed PCA3 mRNAs.

The invention also provides a recombinant nucleic acid molecule comprising a vector and the above-described isolated nucleic acid molecule encoding differentially expressed PCA3 mRNAs.

The invention further provides an antisense nucleic acid molecule specific to the differentially expressed PCA3 mRNAs.

The invention also provides a cell that contains an above-described recombinant nucleic acid molecule.

The invention further relates to a non-human organism that contains an above-described recombinant nucleic acid molecule encoding a differentially expressed PCA3 mRNA. In particular, the invention relates to a non-human organism containing a recombinant nucleic acid molecule encoding a PCA3 mRNA having an additional sequence between exon 3 and exon 4a. In a particularly preferred embodiment, this additional sequence comprises the sequence of SEQ ID NO:1, variants of parts thereof.

The invention also relates to an antibody having binding affinity specifically to a polypeptide encoded by a differentially expressed PCA3 mRNA or an epitope-bearing portion thereof.

The invention further provides a method of detecting differentially expressed PCA3 mRNAs in a sample. As well, it also provides a method of measuring the amount of differentially expressed PCA3 mRNAs in a sample.

The invention further relates to a method of detecting antibodies having binding affinity specifically to polypeptides encoded by a differentially expressed PCA3 mRNA.

In one embodiment, the invention further relates to a diagnostic kit comprising a first container means containing nucleic acid molecules specific for a differentially expressed PCA3 mRNA, and a second container means containing a probe specific to a differentially expressed PCA3 mRNAs.

In another embodiment, the invention relates to a diagnostic kit comprising a first container means containing the above-described antibody, and a second container means containing a conjugate comprising a binding partner of the monoclonal antibody and a label.

The invention also provides a hybridoma which produces the above-described monoclonal antibody.

As well, the invention further relates to diagnostic methods for human disease, in particular, prostate cancer. Preferably, a method of diagnosing the presence or predisposition to develop prostate cancer in a patient is provided herein.

The invention also provides methods for therapeutic uses involving all or part of (1) a nucleic acid sequence encoding the differentially expressed PCA3 mRNAs, variants or parts thereof, (2) antisense to differentially expressed PCA3 mRNA molecules, variants or parts thereof, (3) protein encoded by a differentially expressed PCA3 mRNA, variants or parts thereof, or (4) antibodies to proteins encoded by differentially expressed PCA3 mRNAs.

Further, the invention provides a method to modulate the level of differentially expressed of a first PCA3 mRNA (e.g. the long one) and a second PCA3 mRNA (e.g. the short one) by expressing one of the first or second differentially expressed mRNA. In a preferred embodiment, the invention provides a modulation of the differentially expressed PCA3 mRNAs such that the level of the first PCA3 mRNA is superior to that of the second.

Having identified the differential expression of mRNAs as a marker for prostatic state of an animal, and more particularly having shown that the presence of the additional sequence, which interrupts the coding sequence of the PCA3 encoded protein, correlates with a non-malignant state, while the absence of the additional sequence and a non-interruption of the thereby encoded protein, correlates with malignant cancer, the present invention therefore provides the means to interrupt the coding sequence of the PCA3 protein, using any means of genetic engineering, known to a skilled artisan, and assesses whether such an interruption can revert the malignant phenotype.

In order to provide a clear and consistent understanding of terms used in the present description, a number of definitions are provided hereinbelow.

As used herein, the terminology "non-malignant prostate or status" is meant to cover a non-cancerous prostatic state. Thus, these terminologies are meant to include a normal status as well as a benign prostatic status (such as BPH, for example).

Since the differentiating markers between the malignant and non-malignant prostatic state is at the mRNA and protein level (i.e. an expressed marker), one of the advantages of the present invention is to enable a determination of the prostatic status in an animal using a number of available means to the skilled artisan. Non-limiting examples of such means include nucleic acid probes, antibodies, ligands and PNAs, in easily obtainable cells which express these differentiating markers. A non-limiting example thereof is lymphocytes, thereby enabling a determination from a simple blood sample.

The term "sample" is used herein broadly to refer to all types of samples from an animal in which the differential expression of the short and/or long PCA3 nucleic acid or protein of the present invention can be analyzed. Non-limiting examples thereof include biopsies, blood, fine needle aspirate, urine and bone marrow.

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission.

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals such as for example Sambrook et al. (1989, Molecular Cloning—A Laboratory Manual, Cold Spring Harbor Laboratories) and Ausubel et al. (1994, Current Protocols in Molecular Biology, Wiley, New York).

The present description refers to a number of routinely used recombinant DNA (rDNA) technology terms. Nevertheless, definitions of selected examples of such rDNA terms are provided for clarity and consistency.

As used herein, "nucleic acid molecule", refers to a polymer of nucleotides. Non-limiting examples thereof include DNA (i.e. genomic DNA, cDNA) and RNA molecules (i.e. mRNA). The nucleic acid molecule can be obtained by cloning techniques or synthesized. DNA can be double-stranded or single-stranded (coding strand or non-coding strand [antisense]).

The term "recombinant DNA" as known in the art refers to a DNA molecule resulting from the joining of DNA segments. This is often referred to as genetic engineering.

The term "DNA segment", is used herein, to refer to a DNA molecule comprising a linear stretch or sequence of nucleotides. This sequence when read in accordance with the genetic code, can encode a linear stretch or sequence of amino acids which can be referred to as a polypeptide, protein, protein fragment and the like.

The terminology "amplification pair" refers herein to a pair of oligonucleotides (oligos) of the present invention, which are selected to be used together in amplifying a selected nucleic acid sequence by one of a number of types of amplification processes, preferably a polymerase chain reaction. Other types of amplification processes include ligase chain reaction, strand displacement amplification, or nucleic acid sequence-based amplification, as explained in greater detail below. As commonly known in the art, the oligos are designed to bind to a complementary sequence under selected conditions.

In one particular embodiment, amplification of a nucleic acid sample from a patient is amplified under conditions which favor the amplification of the most abundant differentially expressed nucleic acid. In one preferred embodiment, RT-PCR is carried out on an mRNA sample from a patient under conditions which favor the amplification of the most abundant PCA3 mRNA. In another preferred embodiment, the amplification of the differentially expressed PCA3 nucleic acids is carried out simultaneously. Of course, it will be realized by a person skilled in the art that such methods could be adapted for the detection of differentially expressed proteins instead of differentially expressed nucleic acid sequences.

The nucleic acid (i.e. DNA or RNA) for practicing the present invention may be obtained according to well known methods.

Oligonucleotide probes or primers of the present invention may be of any suitable length, depending on the particular assay format and the particular needs and targeted genomes employed. In general, the oligonucleotide probes or primers are at least 12 nucleotides in length, preferably between 15 and 24 molecules, and they may be adapted to be especially suited to a chosen nucleic acid amplification system. As commonly known in the art, the oligonucleotide probes and primers can be designed by taking into consideration the melting point of hydrizidation thereof with its targeted sequence (see below and in Sambrook et al., 1989, Molecular Cloning—A Laboratory Manual, 2nd Edition, CSH Laboratories; Ausubel et al., 1989, in Current Protocols in Molecular Biology, John Wiley & Sons Inc., N.Y.).

The term "oligonucleotide" or DNA" molecule or sequence refers to a molecule comprised of the deoxyribonucleotides adenine (A), guanine (G), thymine (T) and/or cytosine (C). When in a double-stranded form, it can comprise or include a "regulatory element" according to the present invention, as the term is defined herein. The term "oligonucleotide" or "DNA" can be found in linear DNA molecules or fragments, viruses, plasmids, vectors, chromosomes or synthetically derived DNA. As used herein, particular double-stranded DNA sequences may be described according to the normal convention of giving only the sequence in the 5' to 3' direction. It will also be recognized that "oligonucleotide" can be in a single-stranded form.

"Nucleic acid hybridization" refers generally to the hybridization of two single-stranded nucleic acid molecules having complementary base sequences, which under appropriate conditions will form a thermodynamically favored double-stranded structure. Examples of hybridization conditions can be found in the two laboratory manuals referred above (Sambrook et al., 1989, supra and Ausubel et al., 1989, supra) and are commonly known in the art. In the case of a hybridization to a nitrocellulose filter, as for example in the well known Southern blotting procedure, a nitrocellulose filter can be incubated overnight at 65° C. with a labeled probe in a solution containing 50% formamide, high salt (5×SSC or 5×SSPE), 5×Denhardt's solution, 1% SDS, and 100 μg/ml denatured carrier DNA (i.e. salmon sperm DNA). The non-specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). The selected temperature is based on the melting temperature (Tm) of the DNA hybrid. Of course, RNA-DNA hybrids can also be formed and detected. In such cases, the conditions of hybridization and washing can be adapted according to well known methods by the person of ordinary skill. Stringent conditions will be preferably used (Sambrook et al., 1989, supra).

Probes of the invention can be utilized with naturally occurring sugar-phosphate backbones as well as modified backbones including phosphorothioates, dithionates, alkyl phosphonates and α-nucleotides and the like. Modified sugar-phosphate backbones are generally taught by Miller, 1988, Ann. Reports Med. Chem. 23:295 and Moran et al., 1987, Nucleic acid molecule. Acids Res., 14:5019. Probes of the invention can be constructed of either ribonucleic acid (RNA) or deoxyribonucleic acid (DNA), and preferably of DNA.

The types of detection methods in which probes can be used include Southern blots (DNA detection), dot or slot blots (DNA, RNA), and Northern blots (RNA detection). Although less preferred, labeled proteins could also be used to detect a particular nucleic acid sequence to which it binds. More recently, PNAs have been described (Nielsen et al. 1999, Current Opin. Biotechnol. 10:71-75). PNAs could also be used to detect the mRNAs of the present invention. Other detection methods include kits containing probes on a dipstick setup and the like.

Although the present invention is not specifically dependent on the use of a label for the detection of a particular nucleic acid sequence, such a label might be beneficial, by increasing the sensitivity of the detection. Furthermore, it enables automation. Probes can be labeled according to numerous well known methods (Sambrook et al., 1989, supra). Non-limiting examples of labels include $^3$H, $^{14}$C, $^{32}$P, and $^{35}$S. Non-limiting examples of detectable markers include ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma $^{32}$P ATP and polynucleotide kinase, using the Klenow fragment of Pol I of E. coli in the presence of radioactive dNTP (i.e. uniformly labeled DNA probe using random oligonucleotide primers in low-melt gels), using the SP6/T7 system to transcribe a DNA segment in the presence of one or more radioactive NTP, and the like.

As used herein, "oligonucleotides" or "oligos" define a molecule having two or more nucleotides (ribo or deoxyribonucleotides). The size of the oligo will be dictated by the particular situation and ultimately on the particular use thereof and adapted accordingly by the person of ordinary skill. An oligonucleotide can be synthetised chemically or derived by cloning according to well known methods.

As used herein, a "primer" defines an oligonucleotide which is capable of annealing to a target sequence, thereby creating a double stranded region which can serve as an initiation point for DNA synthesis under suitable conditions.

Amplification of a selected, or target, nucleic acid sequence may be carried out by a number of suitable methods. See generally Kwoh et al., 1990, Am. Biotechnol. Lab. 8:14-25. Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the Qβ replicase system and NASBA (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 1989, supra). Preferably, amplification will be carried out using PCR.

Polymerase chain reaction (PCR) is carried out in accordance with known techniques. See, e.g., U.S. Pat. Nos. 4,683,195; 4,683,202; 4,800,159; and 4,965,188 (the disclosures of all three U.S. Patent are incorporated herein by reference). In general, PCR involves, a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analysed to assess whether the sequence or sequences to be detected are present. Detection of the amplified sequence may be carried out by visualization following EtBr staining of the DNA following gel electrophores, or using a detectable label in accordance with known techniques, and the like. For a review on PCR techniques (see PCR Protocols, A Guide to Methods and Amplifications, Michael et al. Eds, Acad. Press, 1990).

Ligase chain reaction (LCR) is carried out in accordance with known techniques (Weiss, 1991, Science 254:1292). Adaptation of the protocol to meet the desired needs can be carried out by a person of ordinary skill. Strand displacement amplification (SDA) is also carried out in accordance with known techniques or adaptations thereof to meet the particular needs (Walker et al., 1992, Proc. Natl. Acad. Sci. USA 89:392-396; and ibid., 1992, Nucleic Acids Res. 20:1691-1696).

As used herein, the term "gene" is well known in the art and relates to a nucleic acid sequence defining a single protein or polypeptide. A "structural gene" defines a DNA sequence which is transcribed into RNA and translated into a protein having a specific amino acid sequence thereby giving rise the a specific polypeptide or protein. It will be readily recognized by the person of ordinary skill, that the nucleic acid sequence of the present invention can be incorporated into anyone of numerous established kit formats which are well known in the art.

A "heterologous" (i.e. a heterologous gene) region of a DNA molecule is a subsegment segment of DNA within a larger segment that is not found in association therewith in nature. The term "heterologous" can be similarly used to define two polypeptidic segments not joined together in nature. Non-limiting examples of heterologous genes include reporter genes such as luciferase, chloramphenicol acetyl transferase, -galactosidase, and the like which can be juxtaposed or joined to heterologous control regions or to heterologous polypeptides.

The term "vector" is commonly known in the art and defines a plasmid DNA, phage DNA, viral DNA and the like, which can serve as a DNA vehicle into which DNA of the present invention can be cloned. Numerous types of vectors exist and are well known in the art.

The term "expression" defines the process by which a gene is transcribed into mRNA (transcription), the mRNA is then being translated (translation) into one polypeptide (or protein) or more.

The terminology "expression vector" defines a vector or vehicle as described above but designed to enable the expression of an inserted sequence following transformation into a host. The cloned gene (inserted sequence) is usually placed under the control of control element sequences such as promoter sequences. The placing of a cloned gene under such control sequences is often refered to as being operably linked to control elements or sequences.

Operably linked sequences may also include two segments that are transcribed onto the same RNA transcript. Thus, two sequences, such as a promoter and a "reporter sequence" are operably linked if transcription commencing in the promoter will produce an RNA transcript of the reporter sequence. In order to be "operably linked" it is not necessary that two sequences be immediately adjacent to one another.

Expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

Prokaryotic expressions are useful for the preparation of large quantities of the protein encoded by the DNA sequence of interest. This protein can be purified according to standard protocols that take advantage of the intrinsic properties thereof, such as size and charge (i.e. SDS gel electrophoresis, gel filtration, centrifugation, ion exchange chromatography . . . ). In addition, the protein of interest can be purified via affinity chromatography using polyclonal or monoclonal antibodies. The purified protein can be used for therapeutic applications.

The DNA construct can be a vector comprising a promoter that is operably linked to an oligonucleotide sequence of the present invention, which is in turn, operably linked to a heterologous gene, such as the gene for the luciferase reporter molecule. "Promoter" refers to a DNA regulatory region capable of binding directly or indirectly to RNA polymerase in a cell and initiating transcription of a downstream (3' direction) coding sequence. For purposes of the present invention, the promoter is bound at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boses and "CCAT" boxes. Prokaryotic promoters contain −10 and −35 consensus sequences, which serve to initiate transcription and the transcript products contain a Shine-Dalgarno sequence, which serves a ribosome binding sequences during translation initiation.

As used herein, the designation "functional derivative" denotes, in the context of a functional derivative of a sequence whether an nucleic acid or amino acid sequence, a molecule that retains a biological activity (either function or structural) that is substantially similar to that of the original sequence. This functional derivative or equivalent may be a natural derivative or may be prepared synthetically. Such derivatives include amino acid sequences having substitutions, deletions, or additions of one or more amino acids, provided that the biological activity of the protein is conserved. The same applies to derivatives of nucleic acid sequences which can have substitutions, deletions, or additions of one or more nucleotides, provided that the biological activity of the sequence is generally maintained. When relating to a protein sequence, the substituting amino acid as chemico-physical properties which are similar to that of the substituted amino acid. The similar chemico-physical properties include, similarities in charge, bulkiness, hydrophobicity, hydrophylicity and the like. The term "functional derivatives" is intended to include "fragments", "segments", "variants", "analogs" or "chemical derivatives" of the subject matter of the present invention.

Thus, the term "variant" refers herein to a protein or nucleic acid molecule which is substantially similar in structure and biological activity to the protein or nucleic acid of the present invention.

The functional derivatives of the present invention can be synthesized chemically or produced through recombinant DNA technology. All these methods are well known in the art.

As used herein, "chemical derivatives" is meant to cover additional chemical moieties not normally part of the subject matter of the invention. Such moieties could affect the physico-chemical characteristic of the derivative (i.e. solubility, absorption, half life and the like, decrease of toxicity). Such moieties are examplified in Remington's Pharmaceutical Sciences (1980). Methods of coupling these chemical-physical moieties to a polypeptide are well known in the art.

The term "allele" defines an alternative form of a gene which occupies a given locus on a chromosome.

As commonly known, a "mutation" is a detectable change in the genetic material which can be transmitted to a daughter cell. As well known, a mutation can be, for example, a detectable change in one or more deoxyribonucleotide. For example, nucleotides can be added, deleted, substituted for, inverted, or transposed to a new position. Spontaneous mutations and experimentally induced mutations exist. The result of a mutations of nucleic acid molecule is a mutant nucleic acid molecule. A mutant polypeptide can be encoded from this mutant nucleic acid molecule.

As used herein, the term purified refers to a molecule having been separated from a cellular component. Thus, for example, a purified protein has been purified to a level not found in nature. A substantially pure molecule is a molecule that is lacking in all other cellular components.

As used herein, the terms molecule, compound, or agent are used interchangeably and broadly to refer to natural, synthetic or semi-synthetic molecules or compounds. The term molecule therefore denotes for example chemicals, macromolecules, cell or tissue extracts (from plants or animals) and the like. Non limiting examples of molecules include nucleic acid molecules, peptides, ligands, including antibodies, carbohydrates and pharmaceutical agents. The agents can be selected and screened by a variety of means including random screening, rational selection and by rational design using for example protein or ligand modelling methods such as computer modelling. The terms rationally selected or rationally designed are meant to define compounds which have been chosen based on the configuration of the interaction domains of the present invention. As will be understood by the person of ordinary skill, macromolecules having non-naturally occurring modifications are also within the scope of the term molecule. For example, peptidomimetics, well known in the pharmaceutical industry and generally referred to as peptide analogs can be generated by modelling as mentioned above. Similarly, in a preferred embodiment, the polypeptides of the present invention are modified to enhance their stability. It should be understood that in most cases this modification should not alter the biological activity of the protein. The molecules identified in accordance with the teachings of the present invention have a therapeutic value in diseases or conditions in which the physiology or homeastasis of the cell and/or tissue is compromised by a defect in the expression of PCA3 mRNAs. Alternatively, the molecules identified in accordance with the teachings of the present invention find utility in the development of compounds which can modulate the expression of a differentially expressed PCA3 mRNA or modulate the activity or level of a protein encoded thereby.

As used herein, agonists and antagonists also include potentiators of known compounds with such agonist or antagonist properties. In one embodiment, modulators of the level or the activity of the PCA3 protein lacking the additional sequence of the present invention can be identified and selected by contacting the indicator cell with a compound or mixture or library of molecules for a fixed period of time. In certain embodiments, the additional sequence-containing PCA3 protein can serve as a control.

The present invention also provides antisense nucleic acid molecules which can be used for example to decrease or abrogate the expression of the PCA3 mRNA lacking the additional sequence of the present invention or of the protein encoded thereby. An antisense nucleic acid molecule according to the present invention refers to a molecule capable of forming a stable duplex or triplex with a portion of its targeted nucleic acid sequence (DNA or RNA). The use of antisense nucleic acid molecules and the design and modification of such molecules is well known in the art as described for example in WO 96/32966, WO 96/11266, WO 94/15646, WO 93/08845 and U.S. Pat. No. 5,593,974. Antisense nucleic acid molecules according to the present invention can be derived from the nucleic acid sequences and modified in accordance to well known methods. For example, some antisense molecules can be designed to be more resistant to degradation to increase their affinity to their targeted sequence, to affect their transport to chosen cell types or cell compartments, and/or to enhance their lipid solubility by using nucleotide analogs and/or substituting chosen chemical fragments thereof, as commonly known in the art.

An indicator cell in accordance with the present invention can be used to identify antagonists. For example, the test molecule or molecules are incubated with the host cell in conjunction with one or more agonists held at a fixed concentration. An indication and relative strength of the antagonistic properties of the molecule(s) can be provided by comparing the level of gene expression in the indicator cell in the presence of the agonist, in the absence of test molecules vs in the presence thereof. Of course, the antagonistic effect of a molecule can also be determined in the absence of agonist, simply by comparing the level of expression of the reporter gene product in the presence and absence of the test molecule(s).

It shall be understood that the "in vivo" experimental model can also be used to carry out an "in vitro" assay. For example, cellular extracts from the indicator cells can be prepared and used in one of the aforementioned "in vitro" tests.

As used herein the recitation indicator cells refers to cells that express a differentially expressed PCA3 mRNA according to the present invention. In some embodiment, the protein encoded by the nucleic acid sequence can be coupled to an identifiable or selectable phenotype or characteristic. Such indicator cells can be used in the screening assays of the present invention. In certain embodiments, the indicator cells have been engineered so as to express a chosen derivative, fragment, homolog, or mutant of the differentially-expressed PCA3 mRNA of the present invention. The cells can be yeast cells or higher eukaryotic cells such as mammalian cells. When the binding partner for the PCA3 proetin will have been identified, the interaction between the two partners will be able to serve as a target for the modulation of the activity of this PCA3-encoded protein. In one particular embodiment, the indicator cell would be a yeast cell harboring vectors enabling the use of the two hybrid system technology, as well known in the art (Ausubel et al., 1994, supra) and can be used to test a compound or a library thereof. In one embodiment, a reporter gene encoding a selectable marker or an assayable protein can be operably linked to a control element such that expression of the selectable marker or assayable protein is dependent on the interaction of the PCA3-encoded protein and its binding partner. Such an indicator cell could be used to rapidly screen at high-throughput a vast array of test molecules. In a particular embodiment, the reporter gene is luciferase or β-Gal.

In some embodiments, it might be beneficial to express a protein of the present invention as a fusion protein. The design of constructs therefor and the expression and production of fusion proteins and are well known in the art (Sambrook et al., 1989, supra; and Ausubel et al., 1994, supra).

Non limiting examples of such fusion proteins include a hemaglutinin fusions and Gluthione-S-transferase (GST) fusions and Maltose binding protein (MBP) fusions. In certain embodiments, it might be beneficial to introduce a protease cleavage site between the two polypeptide sequences which have been fused. Such protease cleavage sites between two heterologously fused polypeptides are well known in the art.

In certain embodiments, it might also be beneficial to fuse the protein of the present invention to signal peptide sequences enabling a secretion of the fusion protein from the host cell. Signal peptides from diverse organisms are well known in the art. Bacterial OmpA and yeast Suc2 are two non limiting examples of proteins containing signal sequences. In certain embodiments, it might also be beneficial to introduce a linker (commonly known) between the interaction domain and the heterologous polypeptide portion. Such fusion protein find utility in the assays of the present invention as well as for purification purposes, detection purposes and the like.

For certainty, the sequences and polypeptides useful to practice the invention include without being limited thereto mutants, homologs, subtypes, alleles and the like. It shall be understood that generally, the sequences of the present invention should encode a functional (albeit defective) PCA3 protein. It will be clear to the person of ordinary skill that whether the PCA3 of the present invention, variant, derivative, or fragment thereof retains its can be determined by using the teachings and assays of the present invention and the general teachings of the art.

As exemplified herein below, the PCA3 protein of the present invention can be modified, for example by in vitro mutagenesis, to dissect the structure-function relationship thereof and permit a better design and identification of modulating compounds. However, some derivative or analogs having lost their biological function may still find utility, for example for raising antibodies. These antibodies could be used for detection or purification purposes. In addition, these antibodies could also act as competitive or non-competitive inhibitor and be found to be modulators of the activity of the PCA3 protein of the present invention.

A host cell or indicator cell has been "transfected by exogenous or heterologous DNA (e.g. a DNA construct) when such DNA has been introduced inside the cell. The transfecting DNA may or may not be integrated (covalently linked) into chromosomal DNA making up the genome of the cell. In prokaryotes, yeast, and mammalian cells for example, the transfecting DNA may be maintained on a episomal element such as a plasmid. With respect to eukaryotic cells, a stably transfected cell is one in which the transfecting DNA has become integrated into a chromosome so that it is inherited by daughter cells through chromosome replication. This stability is demonstrated by the ability of the eukaryotic cell to establish cell lines or clones comprised of a population of daughter cells containing the transfecting DNA. Transfection methods are well known in the art (Sambrook et al., 1989, supra; Ausubel et al., 1994 supra). The use of a mammalian cell as indicator can provide the advantage of furnishing an intermediate factor, which permits for example the interaction of two polypeptides which are tested, that might not be present in lower eukaryotes or prokaryotes. It will be understood that extracts from mammalian cells for example could be used in certain embodiments, to compensate for the lack of certain factors.

In general, techniques for preparing antibodies (including monoclonal antibodies and hybridomas) and for detecting antigens using antibodies are well known in the art (Campbell, 1984, In Monoclonal Antibody Technology: Laboratory Techniques in Biochemistry and Molecular Biology, Elsevier Science Publisher, Amsterdam, The Netherlands) and in Harlow et al., 1988 (in: Antibody-A Laboratory Manual, CSH Laboratories). The present invention also provides polyclonal, monoclonal antibodies, or humanized versions thereof, chimeric antibodies and the like which inhibit or neutralize their respective interaction domains and/or are specific thereto.

From the specification and appended claims, the term therapeutic agent should be taken in a broad sense so as to also include a combination of at least two such therapeutic agents. Further, the DNA segments or proteins according to the present invention can be introduced into individuals in a number of ways. For example, prostatic cells can be isolated from the afflicted individual, transformed with a DNA construct according to the invention and reintroduced to the afflicted individual in a number of ways. Alternatively, the DNA construct can be administered directly to the afflicted individual. The DNA construct can also be delivered through a vehicle such as a liposome, which can be designed to be targeted to a specific cell type, and engineered to be administered through different routes.

For administration to humans, the prescribing medical professional will ultimately determine the appropriate form and dosage for a given patient, and this can be expected to vary according to the chosen therapeutic regimen (i.e. DNA construct, protein, cells), the response and condition of the patient as well as the severity of the disease.

Composition within the scope of the present invention should contain the active agent (i.e. fusion protein, nucleic acid, and molecule) in an amount effective to achieve the desired therapeutic effect while avoiding adverse side effects. Typically, the nucleic acids in accordance with the present invention can be administered to mammals (i.e. humans) in doses ranging from 0.005 to 1 mg per kg of body weight per day of the mammal which is treated. Pharmaceutically acceptable preparations and salts of the active agent are within the scope of the present invention and are well known in the art (Remington's Pharmaceutical Science, 16th Ed., Mack Ed.). For the administration of polypeptides, antagonists, agonists and the like, the amount administered should be chosen so as to avoid adverse side effects. The dosage will be adapted by the clinician in accordance with conventional factors such as the extent of the disease and different parameters from the patient. Typically, 0.001 to 50 mg/kg/day will be administered to the mammal.

The present invention relates to a kit for diagnosing and/or staging prostate cancer or a predisposition to contracting same comprising a nucleic acid, a protein or a ligand in accordance with the present invention. For example, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample (DNA protein or cells), a container which contains the primers used in the assay, containers which contain enzymes, containers which contain wash reagents, and containers which contain the reagents used to detect the extension products.

The present invention also relates to a kit comprising the oligonucleotide primer of the present invention, which are specific to either one of the PCA3 mRNA lacking the additional sequence of the present invention or the PCA3 mRNA containing the additional sequence of the present invention.

Further objects and advantages of the present invention will be clear from the description that follows.

BRIEF DESCRIPTION OF THE DRAWINGS

Having thus generally described the invention, reference will now be made to the accompanying drawings, showing by way of illustration a preferred embodiment thereof, and in which:

FIG. 3 illustrates the nucleic acid sequences of RT-PCR-amplified PCA3 fragments with and without the additional sequence of the present invention. The sequences were amplifified using PCR primers located in exon 3 and exon 4a. Primer sequences are shown in bold letters. Capital letters represent nucleic acids common to both sequences;

FIG. 4 shows the amino acid sequence predicted from the PCA3 mRNAs containing the additional sequence of the present invention. This sequence corresponds to amino acids 1-23 of the original PCA3 polypeptide; and FIG. 5 shows examples of antigenic epitope-bearing PCA3 peptides comprising 8 amino acids (calculated according to H. G. Rammensee et al., 1995, MHC ligands and peptide motifs: first listing, in Immunogenics; 41(4)). The SEQ ID NOs of the exemplified antigenic epitopes are indicated on the right (SEQ ID NOs 5 to 12).

Figure 1:
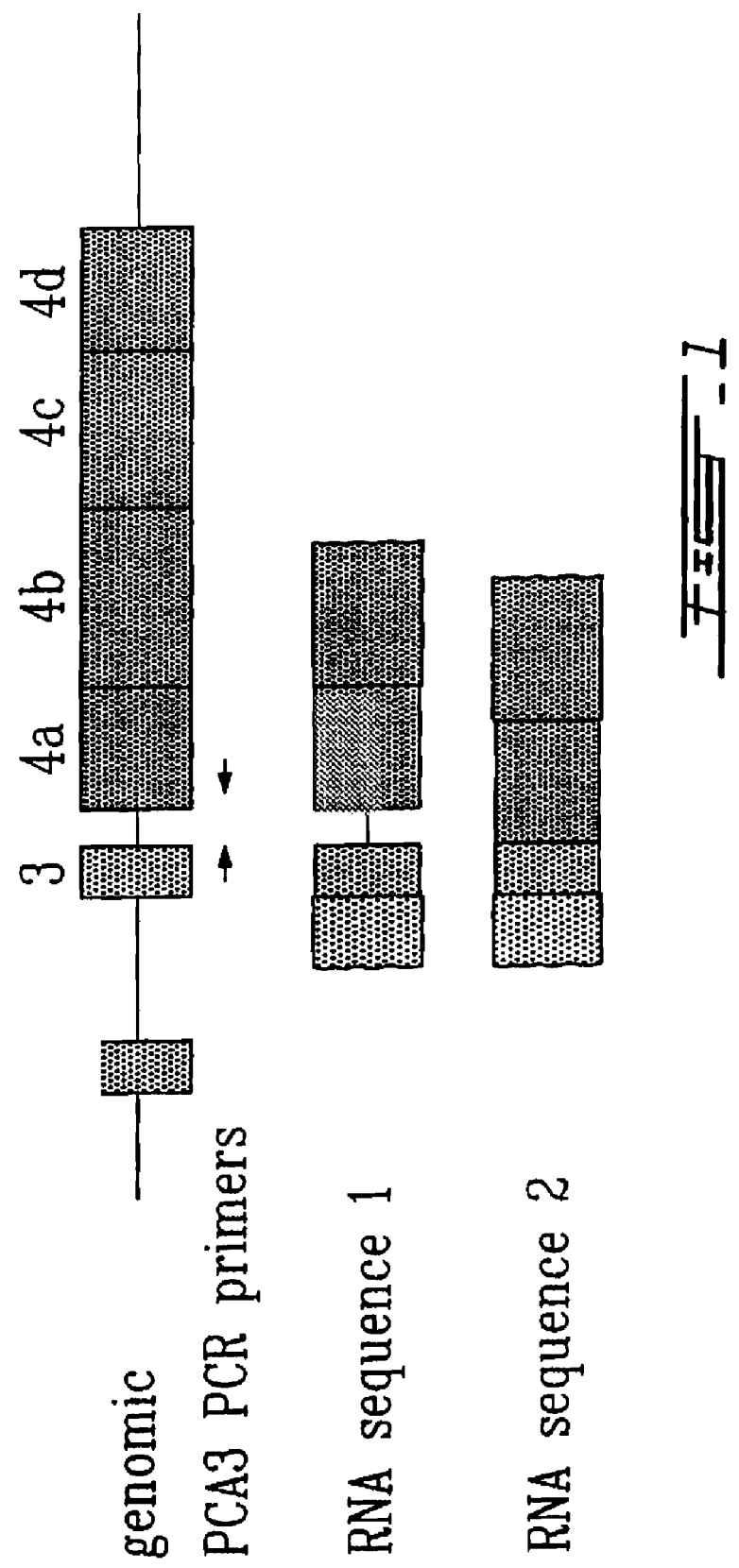
FIG. 1 shows the PCA3 genomic structure and location of oligonucleotides used for PCR.

Other objects, advantages and features of the present invention will become more apparent upon reading of the following non-restrictive description of preferred embodiments with reference to the accompanying drawing which is exemplary and should not be interpreted as limiting the scope of the present invention.

DESCRIPTION OF ILLUSTRATIVE EMBODIMENTS

In one embodiment, the present invention relates to an isolated and/or purified differentially-expressed PCA3 mRNA molecule. Preferably, the PCA3 mRNA or nucleic acid molecule comprises a polynucleotide sequence at least 90% identical (more preferably, 95%, 96%, 97%, 98%, 99% or 100% identical) to a sequence selected from the group consisting of:
(a) a nucleotide sequence encoding a differentially expressed PCA3 polypeptide comprising the complete amino acid sequence in SEQ ID NO: 3;
(b) a nucleotide sequence complementary to any of the nucleotide sequences in (a) or (b).

In one preferred embodiment, the isolated nucleic acid molecule comprises a differentially expressed PCA3 mRNA nucleotide sequence with greater than 90% identity or similarity to the nucleotide sequence present in SEQ ID NO: 1 (preferably greater than 95%, 96%, 97%, 98%, 99% or 100%). In another preferred embodiment, the isolated nucleic acid molecule comprises the differentially expressed PCA3 mRNA sequence lacking the additional sequence present in SEQ ID NO:2. In another embodiment, the isolated differentially expressed additional sequence-minus mRNA sequence nucleic acid molecule encodes the differentially expressed PCA3 amino acid sequence present in SEQ ID NO:3.

Although PCT application CA98/00346 teaches a number of alternatively spliced mRNAs, prior to the present invention, a PCA3 mRNA comprising an additional sequence between exon 3 and exon 4a had not been identified. Furthermore, the identification of this additional sequence as a distinguishing marker of the prostate state had not been made. In addition, the correlation between the PCA3 mRNA minus the additional sequence and prostate cancer (as opposed to the PCA3 mRNA-containing the additional sequence in non-prostate cancer [i.e. normal or BPH]) had not been made. Thus, the additional sequence in PCA3 mRNA enables a prognosis and diagnosis of prostatic diseases in a patient. Preferably, the PCA3 nucleic acid molecule comprises a polynucleotide sequence at least 90% identical (more preferably, 95%, 96%, 97%, 98%, 99% or 100% identical) to one of the above-described differentially expressed mRNAs.

Also included within the scope of this invention are the functional equivalents of the herein-described isolated nucleic acid molecules and derivatives thereof. For example, the nucleic acid sequences depicted in SEQ ID NO:1 and SEQ ID NO:2 can be altered by substitutions, additions or deletions that provide for functionally equivalent molecules. Due to the degeneracy of nucleotide coding sequences, other DNA sequences which encode substantially the same amino acid sequence as depicted in SEQ ID NO: 3 can be used in the practice of the present invention.

In addition, the nucleic acid sequence can comprise a nucleotide sequence which results from the addition, deletion or substitution of at least one nucleotide to the 5'-end and/or the 3'-end of the nucleic acid formula shown in SEQ ID NO:1 or 2 or a derivative thereof. Any nucleotide or polynucleotide can be used in this regard, provided that its addition, deletion or substitution does not substantially alter the amino acid sequence of SEQ ID NO:3 which is encoded by the additional sequence-containing nucleotide sequence. Moreover, the nucleic acid molecule of the present invention can, as necessary, have restriction endonuclease recognition sites added to its 5'-end and/or 3'-end. All variations of the nucleotide sequence of the PCA3 nucleotide coding sequence and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

One skilled in the art will realize that genomes often contain slight allelic variations between individuals. Therefore, the isolated nucleic acid molecule is also intended to include allelic variations, so long as the sequence is a functional derivative of the differentially expressed PCA3 mRNA coding sequence. When a PCA3 allele does not encode the identical sequence to that found in SEQ ID Nos:1 or 2, it can be isolated and identified as PCA3 using the same techniques used herein, and especially PCR techniques to amplify the appropriate gene with primers based on the sequences disclosed herein.

One skilled in the art will realize that organisms other than humans might also contain differentially-expressed PCA3 mRNAs (for example, eukaryotes; more specifically, mammals, birds, fish, and plants; more specifically, gorillas, rhesus monkeys, and chimpanzees). The invention is intended to include, but not be limited to, differentially-expressed PCA3 mRNAs isolated from the above-described organisms.

Isolated nucleic acid molecules of the present invention are also meant to include those chemically synthesized. For example, a nucleic acid molecule with the nucleotide sequence described herein or encoding the herein described differentially expressed products of PCA3 gene can be designed and, if necessary, divided into appropriate smaller fragments. Then an oligomer which corresponds to the nucleic acid molecule, or to each of the divided fragments, can be synthesized. Such synthetic oligonucleotides can be prepared, for example, by the triester method of Matteucci et al., J. Am. Chem. Soc. 103:3185-3191 (1981) or by using an automated DNA synthesizer.

In another embodiment, the present invention relates to purified differentially expressed polypeptides (preferably, substantially pure) having an amino acid sequence corresponding to the herein described PCA3, or a functional derivative thereof. In a preferred embodiment, the polypeptide has the amino acid sequence set forth in SEQ ID NO: 3 or mutant or species variation thereof, or at least 80% identity or at least 90% similarity thereof (preferably, at least 90%, 95%, 96%, 97%, 98%, or 99% identity or at least 95%, 96%, 97%, 98%, or 99% similarity thereof), or at least 6 contiguous amino acids thereof (preferably, at least 10, 15, 20, 25, or 50 contiguous amino acids thereof).

In a preferred embodiment, the invention relates to differentially-expressed PCA3 epitopes. The epitope of these polypeptides is an immunogenic or antigenic epitope. An immunogenic epitope is that part of the protein which elicits an antibody response when the whole protein is the immunogen. An antigenic epitope is a fragment of the protein which can elicit an antibody response. Methods of selecting antigenic epitope fragments are well known in the art. See, Sutcliffe et al., Science 219:660-666 (1983). Antigenic epitope-bearing peptides and polypeptides of the invention are useful to raise an immune response that specifically recognizes the polypeptides. Antigenic epitope-bearing peptides and polypeptides of the invention comprise at least 7 amino acids (preferably, 9, 10, 12, 15 or 20 amino acids) of the proteins of the invention. Examples of an antigenic peptide are shown in FIG. 5 as predicted using the method of Rammensee et al., (1995, MHC ligands and peptide motifs: first listing, in Immunogenics; 41(4)). Of course, it will be realized that other epitope-bearing PCA3 peptides could be predicted and used to raise antibodies.

A variety of methodologies known in the art can be utilized to obtain the peptide of the present invention. In one embodiment, the peptide is purified from tissues or cells which naturally produce the peptide. Alternatively, the above-described isolated nucleic acid fragments can be used to express the differentially expressed PCA3 protein in any organism. The samples of the present invention include cells, protein extracts or membrane extracts of cells, or biological fluids. The sample will vary based on the assay format, the detection method and the nature of the tissues, cells or extracts used as the sample.

Any organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

In another embodiment, the present invention relates to a nucleic acid for the specific detection of the presence of PCA3 nucleic acid in a sample comprising the above-described nucleic acid molecules or at least a fragment thereof which binds under stringent conditions to PCA3 nucleic acid.

In one prefered embodiment, the present invention relates to nucleic acid probes which are complementary to a nucleotide sequence consisting of at least 10 consecutive nucleotides (preferably, 15, 18, 20, 25, or 30) from the nucleic acid molecule comprising a polynucleotide sequence at least 90% identical to a sequence selected from the group consisting of:
(a) a nucleotide sequence encoding the PCA3 polypeptide comprising the complete amino acid sequence in SEQ ID NO: 3;
(b) a nucleotide sequence encoding the PCA3 gene comprising the nucleotide sequence in SEQ ID NO: 1, or 2;
(c) a nucleotide sequence complementary to any of the nucleotide sequences in (a) or (b), and
(d) a nucleotide sequence as previously described above.

In one embodiment of the above described method, a nucleic acid probe is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

In another embodiment, the present invention relates to a method of detecting the presence of differentially expressed PCA3 mRNA in a sample comprising : a) contacting the sample with the above-described nucleic acid probe, under specific hybridization conditions such that hybridization occurs, and b) detecting the presence of the probe bound to the nucleic acid molecule. One skilled in the art would select the nucleic acid probe according to techniques known in the art as described above. Samples to be tested include but should not be limited to RNA samples from human tissue.

Having identified that the additional PCA3 sequence of the present invention can be used as a marker for distinguishing between malignant and non malignant prostate states, probes which are specific to this additional sequence (or variants or fragments thereof) could also be used in accordance with the present invention. Of course, since in certain embodiments, such probes might detect genomic DNA, a positive signal coming from the genomic DNA might have to be eliminated in order to specifically detect the differentially expressed PCA3 mRNA.

Although the present invention is specifically demonstrated using primers hybridizing to exon 3 and exon 4a sequences, it should be clear to the skilled artisan that primers derived from other regions of PCA3 could be used. For example, primers could be derived from sequences of exon 2, exon 4b, exon 4c or to the additional sequence thereof. Methods to derive specific primers from known sequences are well known in the art.

In another embodiment, the present invention relates to a kit for detecting the presence of differentially expressed PCA3 mRNA in a sample comprising at least one container means having disposed therein the above-described nucleic acid probe. In a preferred embodiment, the kit further comprises other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline phosphatase), and affinity labeled probes (biotin, avidin, or steptavidin).

In more detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like.

One skilled in the art will readily recognize that the nucleic acid probes described in the present invention can readily be incorporated into one of the established kit formats which are well known in the art.

In another embodiment of the present invention (and similarly to probes of the present invention) the antibodies of the present invention can be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art. The immobilized antibodies of the present invention can be used for in vitro, in vivo, and in situ assays as well as in immunochromatography.

In another embodiment, the present invention relates to a method of detecting a differentially expressed PCA3 polypeptide in a sample, comprising: a) contacting the sample with an above-described antibody (or protein), under conditions such that immunocomplexes form, and b) detecting the presence of the antibody bound to the polypeptide. In detail, the methods comprise incubating a test sample with one or more of the antibodies of the present invention and assaying whether the antibody binds to the test sample. The relative levels of differentially expressed PCA3 in a sample enable a distiction between a malignant and non-malignant prostatic state.

In a further embodiment, the present invention relates to a method of detecting a PCA3 antibody in a sample, comprising: a) contacting the sample with an above-described differentially expressed PCA3 protein, under conditions such that immunocomplexes form, and b) detecting the presence of the protein bound to the antibody or antibody bound to the protein. In detail, the methods comprise incubating a test sample with one or more of the proteins of the present invention and assaying whether the antibody binds to the test sample.

In another embodiment of the present invention, a kit is provided which contains all the necessary reagents to carry out the previously described methods of detection.

The kit can comprise: i) a first container means containing an above-described antibody, and ii) second container means containing a conjugate comprising a binding partner of the antibody and a label.

The kit can also comprise: i) a first container means containing an above-described protein, and preferably, ii) second container means containing a conjugate comprising a binding partner of the protein and a label. More specifically, a diagnostic kit comprises a differentially expressed PCA3 protein as described above, to detect antibodies in the serum of potentially infected animals or humans.

In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit can be as described above for nucleic acid probe kits.

One skilled in the art will readily recognize that the antibodies described in the present invention can readily be incorporated into one of the established kit formats which are well known in the art.

It is to be understood that although the following discussion is specifically directed to human patients, the teachings are also applicable to any animal that differentially expresses PCA3 mRNAs.

The diagnostic and screening methods of the invention are especially useful for a patient suspected of being at risk for developing a disease associated with an altered expression level of PCA3 based on family history, or a patient in which it is desired to diagnose a PCA3-related disease (ex. prostate cancer).

According to the invention, presymptomatic screening of an individual in need of such screening is now possible using DNA encoding the PCA3 protein or the PCA3 gene of the invention or fragments thereof. The screening method of the invention allows a presymptomatic diagnosis, of the presence of the PCA3-minus additional sequence, differentially expressed PCA3 mRNA in individuals, and thus an opinion concerning the likelihood that such individuals would develop or have developed a PCA3-associated disease or have a normal prostatic state. This is especially valuable for the identification of carriers of altered PCA3 genes, for example, from individuals with a family history of a PCA3-associated disease. Early diagnosis is also desired to maximize appropriate timely intervention.

In one preferred embodiment of the method of screening, a tissue sample would be taken from such individual, and screened for (1) the presence of the PCA3 mRNA lacking the additional sequence of the present invention; (2) the presence of the additional sequence-containing PCA3 mRNA and/or (3) the presence of differentially expressed PCA3 protein. PCA3 mRNA can be characterized and compared to determine differentially expressed PCA3 mRNA (a) levels and/or (b) size. Lastly, differentially expressed PCA3 protein can be (a) detected and/or (b) quantitated using a biological assay for PCA3 activity or using an immunological assay and PCA3 antibodies A presence of a PCA3 mRNA lacking the additional sequence (or an mRNA not modifying and/or not interrupting the PCA3 coding sequence) and/or of the protein encoded thereby would indicate that the patient is at risk for developing prostate cancer, or has developped prostate cancer. A presence of a PCA3 mRNA containing the additional sequence of the present invention and/or of the protein encoded thereby, in the absence of PCA3 mRNA lacking the additional sequence and/or the protein encoded thereby or at a level superior to that of the mRNA lacking the additional sequence and/or the protein encoded thereby would indicate that the patient has not yet developed prostate cancer, and/or has a lower risk of developing prostate cancer.

Therapeutic effects of therapeutic nucleic acids can include, but are not limited to turning off or modifying the processing of the differentially expressed PCA3 mRNA lacking the additional sequence of the present invention. In addition, an expression of a differentially-expressed PCA3 mRNA comprising the additional sequence in accordance with the present invention to a higher level than that of the PCA3 mRNA lacking the additional sequence could have cancer-reversing effects on cells.

Included as well in the invention are pharmaceutical compositions comprising an effective amount of at least one antisense oligonucleotide to a PCA3 mRNA lacking the additional sequence, in combination with a pharmaceutically acceptable carrier. Such antisense oligos include, but are not limited to, at least one nucleotide sequence of 12-500 bases in length which is complementary to at least a portion of SEQ ID NO:2.

Thus, broadly, the invention provides means to shift the balance between the quantity of the differentially expressed PCA3 mRNAs such that the malignant state of a cell can be modulated.

Specificity for gene expression in prostate cancer cells can be conferred by using appropriate cell-specific regulatory sequences, such as cell-specific enhancers and promoters. Thus, gene therapy can be used to alleviate PCA3 related pathology by inhibiting the inappropriate expression of a particular form of PCA3. Moreover, gene therapy can be used to alleviate such pathologies by providing the appropriate expression level of a particular form of PCA3. In this case, particular PCA3 nucleic acid sequences can be coded by DNA or RNA constructs which are administered in the form of viruses, as described above.

The present invention provides the above-described PCA3 antibodies (preferably, PCA3 murine antibodies and chimeric PCA3 murine-human antibodies, and fragments and regions thereof) which inhibit or neutralize PCA3 biological activity in vivo and are specific for PCA3. These antibodies can be used for therapeutic purposes in subjects having pathologies or conditions associated with the presence of aberrant PCA3 expression. Antibodies, and fragments, regions and derivatives thereof, of the present invention preferably contain at least one region which recognizes an epitope of PCA3 which has inhibiting and/or neutralizing biological activity in vivo.

Treatment comprises parenterally administering a single or multiple doses of the antibody, fragment or derivative. Preferred for human pharmaceutical use are high affinity potent PCA3-inhibiting and/or neutralizing murine and chimeric antibodies, fragments and regions of this invention.

Monoclonal antibodies of the present invention may be administered by any means that enables the active agent to reach the agent's site of action in the body of a mammal. Because proteins are subject to being digested when administered orally, parenteral administration, i.e., intravenous, subcutaneous, intramuscular, would ordinarily be used to optimize absorption.

Monoclonal antibodies of the present invention may be administered either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (composition) suitable for internal administration generally contain from about 1 milligram to about 500 milligrams of active ingredient per unit. In these pharmaceutical compositions the active ingredient will ordinarily be present in an amount of about 0.5-95% by weight based on the total weight of the composition.

Cytotoxic drugs which can be conjugated to antibodies and subsequently used for in vivo therapy include, but are not limited to, daunorubicin, doxorubicin, methotrexate, and Mitomycin C.

The non-human animals of the invention comprise any animal having a transgenic interruption or alteration of the endogenous gene(s) (knock-out animals) and/or into the genome of which has been introduced one or more transgenes that direct the expression of diffrentially expressed human PCA3 mRNAs. Also prefered are the introduction of antisense PCA3 nucleic acids.

Such non-human animals include vertebrates such as rodents, non-human primates, sheep, dog, cow, amphibians, reptiles, etc. Preferred non-human animals are selected from non-human mammalian species of animals, most preferably, animals from the rodent family including rats and mice, most preferably mice.

The transgenic animals of the invention are animals into which has been introduced by nonnatural means (i.e., by human manipulation), one or more genes that do not occur naturally in the animal, e.g., foreign genes, genetically engineered endogenous genes, etc. The nonnaturally introduced genes, known as transgenes, may be from the same or a different species as the animal but not naturally found in the animal in the configuration and/or at the chromosomal locus conferred by the transgene. Transgenes may comprise foreign DNA sequences, i.e., sequences not normally found in the genome of the host animal. Alternatively or additionally, transgenes may comprise endogenous DNA sequences that are abnormal in that they have been rearranged or mutated in vitro in order to alter the normal in vivo pattern of expression of the gene, or to alter or eliminate the biological activity of an endogenous gene product encoded by the gene.

The transgenic non-human animals of the invention are produced by introducing transgenes into the germline of the non-human animal. Embryonic target cells at various developmental stages are used to introduce the transgenes of the invention. Different methods are used depending on the stage of development of the embryonic target cell(s). These methods are well known in the art.

Transgenes may be introduced into non-human animals in order to provide animal models for human diseases. Transgenes that result in such animal models include, e.g., transgenes that encode the differentially expressed PCA3 mRNAs associated with a malignant prostate status (i.e., prostate cancer) or a non-malignant prostate status.

Having identified a marker sequence in differentially expressed PCA3 mRNA and a correlation between the balance of the expression level of the differentially expressed PCA3 mRNAs (or protein encoded thereby) and the malignant or non-malignant prostatic states, the present invention opens the way to numerous methods, assays and reagents for the prognosis, diagnosis, staging, predisposition and therapy of prostate cancer. In a broad embodiment, the present invention provides the means to assess prostate cancer by identifying PCA3 mRNA lacking the additional sequence in accordance with the present invention (or a protein encoded thereby). Numerous methods, primers, probes, antibodies and reagents can be used to identify such a nucleic acid molecule (or such a protein), as will be clear to the skilled artisan to which the present invention pertains.

The present invention is illustrated in further detail by the following non-limiting examples.

EXAMPLE 1

Figure 2:
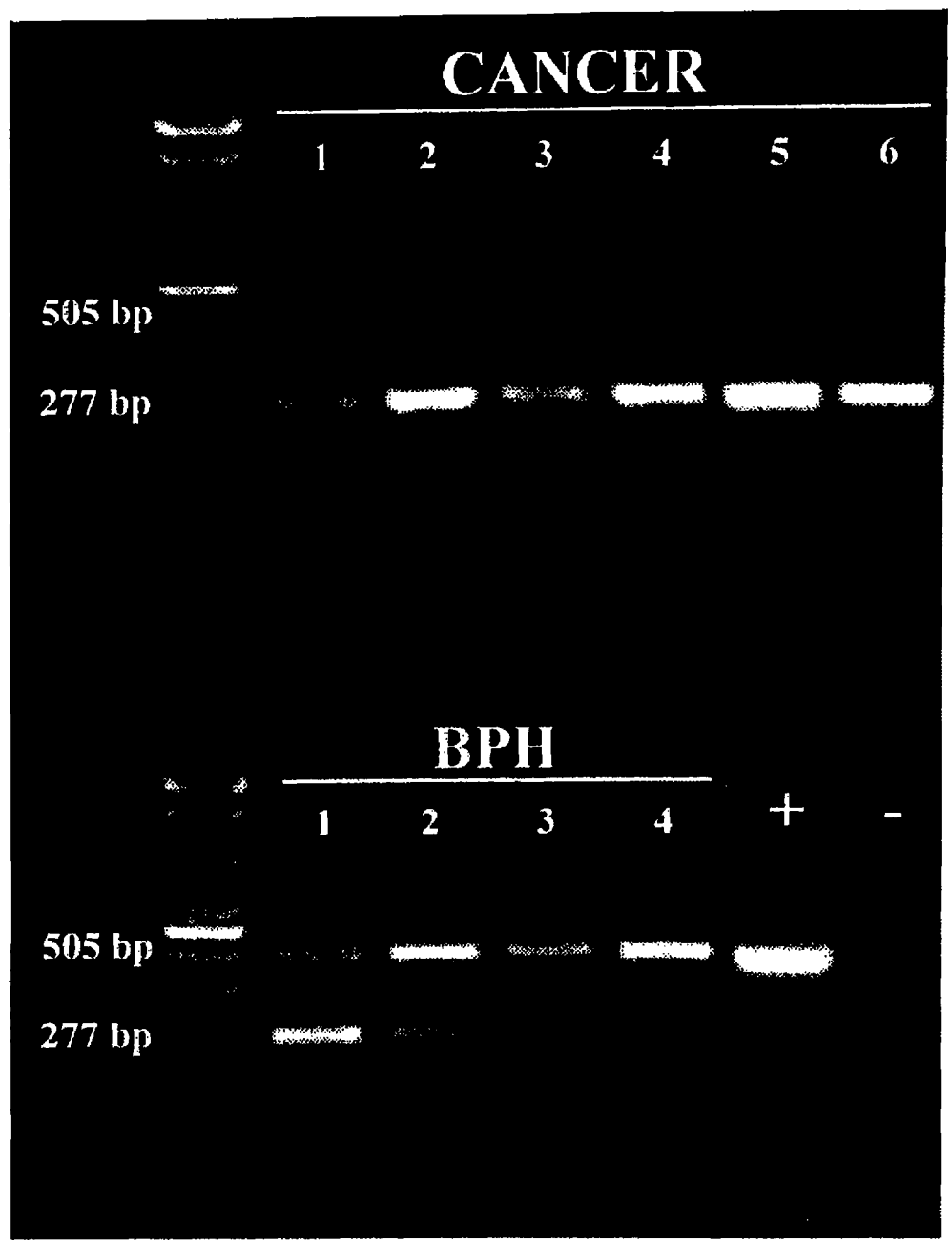
FIG. 2 shows a gel separating PCA3 RT-PCR products amplified from tissue biopsies of prostate cancer and benign prostate hyperplasia, using the primers of Example 1.

Identification of Differentially Expressed PCA3 mRNAs and Correlation of Their Expression with Prostatic Disease PCA3-specific PCR primers were developed in order to analyze PCA3 expression in different samples. To be able to discern between sequences amplified from mRNA (messenger RNA) and genomic DNA, these primers were designed to span an intron, in occurence intron 3. As illustrated in FIG. 1, the PCA3 sense primer lies within exon 3 and the PCA3 antisense primer within exon 4a. Samples to be analyzed for PCA3 expression consisted of frozen tissue chips removed by transurethral resection of the prostate (BPH, 4 patients) or frozen prostates obtained by radical prostatectomy (prostate cancer, 6 patients). Radical prostatectomy samples were processed into frozen sections to specifically select regions containing prostate cancer cells. RNA was extracted from the frozen samples using a liquid-phase RNA extraction method (Trizol™). Extracted nucleic acids were subsequently treated with DNase in order to digest genomic DNA. DNase-treated RNA was reverse transcribed into cDNA using reverse transcriptase and then submitted to PCR-analysis using the PCA3 primers. PCR was performed for 35 cycles with Taq DNA polymerase, amplified material was separated on agarose gels and visualized by ethidium bromide staining. As shown in FIG. 2, PCR amplification of PCA3 generates two products which can be separated by size and differ in relative abundancy. The smaller amplicon (277 bp) is predominantly or exclusively found in samples from prostate cancer patients (FIG. 2, upper row) whereas the larger amplicon (505 bp) is more prominent in samples from patients with a non-malignant prostatic state (BPH [FIG. 2, lower row]). Pathological examination of patients' biopsies confirmed the initial diagnosis for each patient except for Patient BPH 1 which was found to have prostate cancer.

In order to confirm the origin of the amplified fragments, they were isolated from the gel and sequenced. Sequences are shown in FIG. 3. As expected, the smaller 277 by fragment proved to correspond to the regions of exons 3 and 4a spanned by the PCA3 PCR primers. The larger 505 by fragment is identical to the smaller fragment except for the herein identified sequence which lies between exon 3 and exon 4a. Of note, direct PCR analysis of all samples without reverse transcription did not yield amplified material ruling out the hypothesis that the larger amplification product originates from genomic DNA.

Thus, PCA3 mRNA is present in at least two distinct forms within the cell, a short form lacking the herein identified additional sequence (hereafter called sequence 2; SEQ ID NO:2) as well as a long form having this additional sequence (hereafter called sequence 1; SEQ ID NO:1). The presence of the additional sequence in sequence 1 interrupts the predicted open reading frame coding for the PCA3 protein. The predicted sequence of the protein encoded by this long PCA3 mRNA is shown in FIG. 4. As illustrated in FIG. 2, relative expression levels of the two PCA3 mRNA sequences vary dependent on the cell type. Prostate cancer cells predominantly express sequence 2 whereas BPH cells mainly express sequence 1.

These observations demonstrate that it is possible to discern between a malignant and non-malignant state of a prostate. As well, it is tempting to predict that the relative levels of the two types of PCA3 mRNAs, will enable to discern the benign state from the malignant state.

EXAMPLE 2

Assessment of the Prostatic State of a Patient Using RT-PCR

Patient samples were obtained and RNA prepared therefrom as commonly known. Reverse transcription mixes were prepared as RT follows: 0.2 pg total RNA+0.6 µg pdN6 (random hexamer primers)+1.25 mM dNTPs+200 U M-MLV reverse transcriptase in 50 mM Tris-HCl pH 8.3, 75 mM KCl, 3 mM $MgCl_2$, 10 mM DTT. The mixture was incubated 1 hr at 40° C.

4 µl of the RT-reaction of above was mixed in 50 µL of 20 mM Tris-HCl pH 8.4, 50 mM KCl, 2.5 mM $MgCl_2$, 0.5 mM dNTPs, 0.5 µM of each primer and 2.5 U Taq DNA polymerase. For PCR analysis, the amplification was carried out for 35 cycles (1 min each at 94° C., 60° C., 72° C.) followed by a 10 min extension at 72° C. The PCR products were analyzed by conventional agarose gel electrophoresis.

Although the present invention has been described hereinabove by way of preferred embodiments thereof, it can be modified, without departing from the spirit and nature of the subject invention as defined in the appended claims.

What is claimed is:

1. A method of determining the malignancy status of prostate cells contained in a sample undergoing testing, said method comprising:
   (a) amplifying PCA3 nucleic acids using RNA templates and a pair of oligonucleotides which amplify across nucleotide positions 26 and 255 of SEQ ID NO:1 and across nucleotide positions 26 and 27 of SEQ ID NO:2, thereby resulting in a collection of amplified nucleic acids, when said PCA3 nucleic acids are present, said collection comprising
      (i) a PCA3 nucleic acid that comprises an additional sequence between PCA3 exon 3 and PCA3 exon 4a, said additional sequence consisting essentially of nucleotides 27 to 254 of SEQ ID NO:1; and
      (ii) a PCA3 nucleic acid that comprises PCA3 exon 3 joined to PCA3 exon 4a without including said additional sequence; and
   (b) detecting among said collection of amplified nucleic acids
      (iii) substantially only said PCA3 nucleic acid that comprises PCA3 exon 3 joined to PCA3 exon 4a without including said additional sequence, and not said PCA3 nucleic acid that comprises said additional sequence, if said sample comprises prostate cancer cells; and
      (iv) substantially only said PCA3 nucleic acid that comprises said additional sequence between PCA3 exon 3 and PCA3 exon 4a, and not said PCA3 nucleic acid that comprises PCA3 exon 3 joined to PCA3 exon 4a without including said additional sequence, if prostate cells contained in the sample consist of benign prostate cells associated with BPH,
   thereby determining the malignancy status of prostate cells contained in said sample.

2. The method of claim 1, wherein said pair of oligonucleotides comprises a first oligonucleotide which binds to or upstream of nucleotide position 26 of SEQ ID NO:1, and a second oligonucleotide which binds to or downstream of nucleotide position 255 of SEQ ID NO:1.

3. The method of claim 1, wherein said pair of oligonucleotides comprises a first oligonucleotide which binds to exon 3 and a second oligonucleotide which binds to exon 4a.

4. The method of claim 1, wherein after step (a) and before step (b) there is an additional step of contacting said amplified nucleic acids with a detectably labelled hybridization probe.

5. The method of claim 4, wherein said detecting in step b) comprises binding with a probe which hybridizes under high stringency conditions to at least 10 consecutive nucleotides of a sequence comprising nucleotides 26 and 27 of SEQ ID NO:2, which define the exon 3-exon 4a junction, wherein said high stringency conditions comprise a hybridization at 65° C. in 5×SSC, 5×Denhardt's solution, 1% SDS, and 100 µg/ml denatured salmon sperm DNA.

6. The method of claim 5, wherein said probe hybridizes to at least 15 consecutive nucleotides of said exon 3-exon 4a junction.

7. The method of claim 5, wherein said probe hybridizes to at least 20 consecutive nucleotides of said exon 3-exon 4a junction.

8. The method of claim 4, wherein said probe hybridizes to at least 15 consecutive nucleotides of said exon 3-exon 4a junction.

9. The method of claim 4, wherein said probe hybridizes to at least 20 consecutive nucleotides of said exon 3-exon 4a junction.

10. The method of claim 1, wherein said oligonucleotides are at least 10 nucleotides in length.

11. The method of claim 1, wherein said amplifying in step (a) comprises a reaction selected from the group consisting of a nucleic acid sequence-based amplification reaction (NASBA), a polymerase chain reaction (PCR), a transcription-based amplification reaction, a strand displacement amplification (SDA), a ligase chain reaction (LCR), and a Qβ replicase reaction.

12. The method of claim 1, wherein said oligonucleotides are at least 12 nucleotides in length.

13. The method of claim 1, wherein said oligonucleotides are at least 15 nucleotides in length.

14. The method of claim 1, wherein said oligonucleotides are at least 20 nucleotides in length.

15. The method of claim 1, wherein said oligonucleotides are at least 18 to about 50 nucleotides in length.

16. The method of claim 1, wherein said oligonucleotides are at least 20 to about 35 nucleotides in length.

17. The method of claim 1, wherein said pair of oligonucleotides comprises a first oligonucleotide binding to a sequence comprised in nucleotides 1 to 26 of SEQ ID NO:1, and a second oligonucleotide binding to a sequence comprised in nucleotides 255 to 506 of SEQ ID NO:1.

18. A method of distinguishing differentially expressed PCA3 nucleic acids that indicate the malignancy status of prostate cells contained in a sample undergoing testing, said method comprising:
   (a) performing a nucleic acid amplification reaction, using RNAs obtained from prostate cells contained in said sample as templates to amplify PCA3 nucleic acid sequences across nucleotide positions 26 and 255 of SEQ ID NO:1, which respectively define the PCA3 exon 3-intron 3 and intron 3-exon 4a junctions, and nucleotide positions 26 and 27 of SEQ ID NO:2, which define the PCA3 exon 3-exon 4a junction, whereby there are synthesized first and second amplification products;
   wherein said first amplification product results from an amplification of a first PCA3 RNA that comprises portions of exon 3 and exon 4a sequences and an additional sequence between PCA3 exon 3 and PCA3 exon 4a, said additional sequence consisting essentially of nucleotides 27 to 254 of SEQ ID NO:1, and
   wherein said second amplification product results from an amplification of a second PCA3 RNA that comprises portions of exon 3 and exon 4a sequences with PCA3 exon 3 joined to PCA3 exon 4a without including said additional sequence; and
   (b) detecting one of said first and second amplification products independent of the other, thereby distinguishing differentially expressed PCA3 nucleic acids that indicate the status of prostate cells contained in said sample.

19. The method of claim 18, wherein said amplification is carried-out with a pair of oligonucleotides comprising a first oligonucleotide which binds to exon 3 and a second oligonucleotide which binds to exon 4a.

20. A kit for determining the malignancy status of prostate cells by distinguishing between a non-malignant PCA3 nucleic acid and a malignant PCA3 nucleic acid in a sample undergoing testing said kit comprising:
   (a) a pair of oligonucleotides which amplify across nucleotide positions 26 and 255 of SEQ ID NO:1 and across nucleotide positions 26 and 27 of SEQ ID NO:2, thereby resulting in a collection of amplified nucleic acids, when said PCA3 nucleic acids are present, said collection comprising a PCA3 nucleic acid that comprises an additional sequence between PCA3 exon 3 and PCA3 exon 4a, said additional sequence consisting essentially of nucleotides 27 to 254 of SEQ ID NO:1, and a PCA3 nucleic acid that comprises PCA3 exon 3 joined to PCA3 exon 4a without including said additional sequence; and (b) a probe hybridizing under high stringency conditions to at least 10 consecutive nucleotides of a nucleic acid comprising nucleotide positions 26 and 27 of SEQ ID NO:2, which define the PCA3 exon 3-exon 4a junction, thereby detecting among said collection of amplified nucleic acids substantially only said PCA3 nucleic acid that comprises PCA3 exon 3 joined to PCA3 exon 4a without including said additional sequence, and not said PCA3 nucleic acid that comprises said additional sequence.

* * * * *